US012383368B2

(12) United States Patent
Liu

(10) Patent No.: US 12,383,368 B2
(45) Date of Patent: Aug. 12, 2025

(54) IMAGING AND DISPLAY SYSTEM FOR GUIDING MEDICAL INTERVENTIONS

(71) Applicant: Yang Liu, Iowa City, IA (US)

(72) Inventor: Yang Liu, Iowa City, IA (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 18/244,052

(22) Filed: Sep. 8, 2023

(65) Prior Publication Data
US 2023/0414311 A1 Dec. 28, 2023

Related U.S. Application Data

(63) Continuation of application No. 17/106,834, filed on Nov. 30, 2020, now Pat. No. 11,751,971, which is a continuation of application No. 15/118,139, filed as application No. PCT/US2014/062468 on Oct. 27, 2014, now Pat. No. 10,849,710.
(Continued)

(51) Int. Cl.
*A61B 5/05* (2021.01)
*A61B 90/00* (2016.01)
*A61B 90/20* (2016.01)
*A61B 34/20* (2016.01)
(Continued)

(52) U.S. Cl.
CPC .............. *A61B 90/37* (2016.02); *A61B 90/00* (2016.02); *A61B 90/20* (2016.02); *A61B 90/36* (2016.02); *A61B 2034/2048* (2016.02); *A61B 2034/2051* (2016.02); *A61B 2034/2055* (2016.02); *A61B 2090/309* (2016.02); *A61B 2090/365* (2016.02); *A61B 2090/371* (2016.02); *A61B 2090/372* (2016.02); *A61B 2090/3735* (2016.02);
(Continued)

(58) Field of Classification Search
CPC ......... A61B 90/00; A61B 90/20; A61B 90/36; A61B 2090/309; A61B 2090/365; A61B 2090/371; A61B 2090/372; A61B 2090/3941
See application file for complete search history.

(56) References Cited

U.S. PATENT DOCUMENTS 10,013,777 B2  7/2018 Mariampillai et al.
10,548,672 B2  2/2020 Yang et al.
(Continued)

*Primary Examiner* — Joel F Brutus
(74) *Attorney, Agent, or Firm* — RENNER KENNER GREIVE BOBAK TAYLOR & WEBER

(57) ABSTRACT

An imaging and display system for guiding medical interventions includes a wearable display, such as a goggle display, for viewing by a user. The display presents a composite, or combined image that includes pre-operative surgical navigation images, intraoperative images, and in-vivo microscopy images or sensing data. The pre-operative images are acquired from scanners, such as MRI and CT scanners, while the intra-operative images are acquired in real-time from a camera system carried by the goggle display for imaging the patient being treated so as to acquire intraoperative images, such as fluorescence images. A probe, such as a microscopy probe or a sensing probe, is used to acquire in-vivo imaging/sensing data from the patient. Additionally, the intra-operative and in-vivo images are acquired using tracking and registration techniques to align them with the pre-operative image and the patient to form a composite image for display by the goggle display.

20 Claims, 8 Drawing Sheets

Related U.S. Application Data

(60) Provisional application No. 61/942,666, filed on Feb. 21, 2014.

(51) Int. Cl.
    *A61B 90/30*     (2016.01)
    *A61B 90/50*     (2016.01)

(52) U.S. Cl.
    CPC ........... *A61B 2090/3762* (2016.02); *A61B 2090/3941* (2016.02); *A61B 2090/502* (2016.02)

(56) References Cited

U.S. PATENT DOCUMENTS

| | | | |
|---|---|---|---|
| 2007/0160279 A1* | 7/2007 | Demos | A61B 5/0071 359/368 |
| 2008/0013809 A1* | 1/2008 | Zhu | G16H 20/40 382/128 |
| 2010/0245557 A1* | 9/2010 | Luley, III | G02B 21/0012 359/368 |
| 2011/0090233 A1* | 4/2011 | Shahraray | G02B 30/24 345/520 |
| 2011/0144462 A1* | 6/2011 | Lifsitz | A61B 5/0059 600/323 |

\* cited by examiner

IMAGING AND DISPLAY SYSTEM FOR GUIDING MEDICAL INTERVENTIONS

CROSS-REFERENCE TO RELATED APPLICATION

This application is a continuation application of prior application Ser. No. 17/106,384 filed Nov. 30, 2020, issuing as U.S. Pat. No. 11,751,971 on Sep. 12, 2023, which is a continuation application of prior application Ser. No. 15/118,139 filed Aug. 11, 2016, issued as U.S. Pat. No. 10,849,710 on Dec. 1, 2020, which is a 371 application of PCT/US2014/062468 filed Oct. 27, 2014, which claims the benefit of U.S. provisional application No. 61/942,666 filed Feb. 21, 2014, which are incorporated by reference.

TECHNICAL FIELD

The present invention generally relates to imaging and display systems. Particularly, the present invention relates to an imaging and display system for guiding medical interventions, such as surgical interventions. More particularly, the present invention relates to a wearable imaging and display system for guiding medical interventions by the simultaneous display of pre-operative surgical navigation images, real-time intra-operative images, and in-vivo, microscopy imaging and sensing data.

BACKGROUND OF THE INVENTION

Medical professionals, such as surgeons, face enormous challenges during surgical interventions. To assist surgeons in their efforts to provide efficient and effective surgical care, three independent and separate approaches for guiding medical or surgical interventions, or providing medical or surgical guidance, are currently used.

The first approach for providing surgical guidance is typically referred to as "conventional" surgical navigation, and involves the use of pre-operative images of a target of interest (TOI), such as brain tumor images for example, which are captured before surgery takes place. In addition to the use of pre-operative images, surgical navigation tracks the position of surgical instruments relative to these pre-operative images, allowing the surgeon to view the movement of the surgical instruments relative to the pre-operative images. In other words, surgical navigation provides a visual display for the surgeon, whereupon the location and movement of the surgical tools relative to the pre-operative images is displayed for the benefit of the surgeon. The pre-operative images may include various image types, including X-ray computed tomography (CT) images or magnetic resonance imaging (Mill) for example.

The second approach of providing surgical guidance includes the use of intra-operative images, which are images that are acquired, in real-time, while a surgical procedure is being performed on a patient. For example, fluoroscopy and ultrasound are two well-known intraoperative imaging technologies that are used for providing intra-operative based surgical navigation. There has also been a desire from the surgical community for the use of optical imaging when providing intra-operative surgical guidance.

The third approach of surgical guidance is based on using a microscopy/pathology report. For example, in the case of tumor resection, the surgeon will selectively remove a tissue specimen from a target tissue and send it to a pathologist for analysis. During analysis, the tissue is sectioned, stained and examined under a microscope, whereupon the pathologist advises the surgeon as to whether there are any residual cancerous cells in the tissue.

However, conventional surgical navigation, intra-operative imaging-based medical guidance, and pathology-based medical guidance techniques have a variety of drawbacks. For example, because conventional surgical navigation is based on pre-operative images, it is therefore unable to accommodate the tissue deformation that occurs at the surgical site during the performance of the surgical procedure; and is unable to provide real-time imaging updates. In addition, real-time intra-operative imaging surgical guidance techniques provides a limited field of view of the surgical site to the surgeon, and is unable to provide comprehensive, global, whole-body anatomical information of a patient, which makes such surgical guidance techniques difficult to use in some instances. Furthermore, pathology/microscopy-based techniques are unable to sample all surgical sites, and also requires a substantial amount of time to complete.

Therefore, there is a need for an imaging and display system for guiding medical interventions, which provides surgical navigation, intra-operative medical guidance, and in-vivo microscopy medical guidance (i.e. pathology surgical guidance), simultaneously, at the same time. In addition, there is a need for an imaging and display system for guiding medical interventions, which provides a wearable display device, such as a wearable goggle-type display, for displaying the surgical navigation images, the real-time intra-operative images, and the in-vivo imaging/sensing (e.g. microscopy images or spectroscopy data) data at the same time, to thereby provide an immersive, 3D, stereoscopic view, which imparts a natural sense of depth to the images viewed by the surgeon wearing the display device. In addition, there is a need for an imaging and display system for guiding medical interventions, which provides the ability to communicate via a communication network, so as to collaborate and share surgical guidance related images and any other data with any other computer device in communication with the network, such as smart phones, laptop computers and the like.

SUMMARY OF THE INVENTION

In a first embodiment, the present invention provides an imaging and display system for guiding medical interventions comprising: a display adapted to be worn by a user; a detector coupled to said display, said detector configured to capture intra-operative images from a target; and a computing unit coupled to said display and to said detector, said computing unit adapted to store pre-operative images.

In a second embodiment, the present invention provides an imaging and display system as in the first embodiment, wherein said display presents said pre-operative image and said intra-operative image simultaneously.

In a third embodiment, the present invention provides an imaging and display system as in the first embodiment, wherein said display presents said pre-operative image and said intra-operative image simultaneously as a composite, co-registered image on said display.

In a fourth embodiment, the present invention provides an imaging and display system as in the first embodiment, further comprising: a communication interface coupled to said computing unit to enable communication with at least one other display.

In a fifth embodiment, the present invention provides an imaging and display system as in the first embodiment, further comprising: a peripheral interface coupled to said computing unit, said peripheral interface adapted to communicate with one or more peripherals.

In a sixth embodiment, the present invention provides an imaging and display system as in the first embodiment further comprising: a peripheral interface coupled to said computing device, said peripheral interface adapted to communicate with one or more peripherals, wherein said peripheral comprises a microscope (in vivo, hand-held or conventional) selected from the group consisting of: a fiber microscope, a handheld microscope, a color microscope, a reflectance microscope, a fluorescence microscope, an oxygen-saturation microscope, a polarization microscope, an infrared microscope, an interference microscope, a phase contrast microscope, a differential interference contrast microscope, a hyperspectral microscope, a total internal reflection fluorescence microscope, a confocal microscope, a non-linear microscope, a 2-photon microscope, a second-harmonic generation microscope, a super-resolution microscope, a photoacoustic microscope, a structured light microscope, a 4Pi microscope, a stimulated emission depletion microscope, a stochastic optical reconstruction microscope, an ultrasound microscope, and combinations thereof.

In a seventh embodiment, the present invention provides an imaging and display system as in the first embodiment, further comprising: a peripheral interface coupled to said computing device, said peripheral interface adapted to communicate with one or more peripherals, wherein said one or more peripherals comprises a imaging system selected from the group consisting of: an ultrasound imager, a reflectance imager, a diffuse reflectance Imager, a fluorescence imager, a Cerenkov imager, a polarization imager, a radiometric imager, an oxygen saturation imager, an optical coherence tomography imager, an infrared imager, a thermal imager, a photoacoustic imager, a spectroscopic imager, a Raman spectroscopic imager, a hyper-spectral imager, a fluoroscopic imager, a gamma imager, an X-ray computed tomography imager, an endoscope imager, a laparoscope imager, a bronchoscope imager, an angioscope imager, and an imaging catheter imager.

In an eighth embodiment, the present invention provides an imaging and display system as in the first embodiment further comprising: a peripheral interface coupled to said computing device, said peripheral interface adapted to communicate with one or more peripherals, wherein said peripheral comprises a spectrometer selected from the group consisting of: an optical spectrometer, an absorption spectrometer, a fluorescence spectrometer, a Raman spectrometer, a coherent anti-stokes Raman spectrometer, a surface-enhanced Raman spectrometer, a Fourier transform spectrometer, a Fourier transform infrared spectrometer (FTIR), a diffuse reflectance spectrometer, a multiplex or frequency-modulated spectrometer, an X-ray spectrometer, an attenuated total reflectance spectrometer, an electron paramagnetic spectrometer, an electron spectrometer, a gamma-ray spectrometer, an acoustic resonance spectrometer, an auger spectrometer, a cavity ring down auger spectrometer, a circular dichroism auger spectrometer, a cold vapour atomic fluorescence auger spectrometer, a correlation spectrometer, a deep-level transient spectrometer, a dual polarization interferometry, an EPR spectrometer, a force spectrometer, a Hadron spectrometer, a Baryon spectrometer, a meson spectrometer, an nelastic electron tunneling spectrometer (IETS), a laser-induced breakdown spectrometer (LIBS), a mass spectrometer, a Mossbauer spectrometer, a neutron spin echo spectrometer, a photoacoustic spectrometer, a photoemission spectrometer, a photothermal spectrometer, a pump-probe spectrometer, a Raman optical activity spectrometer, a saturated spectrometer, a scanning tunneling spectrometer, a spectrophotometry spectrometer, time-resolved spectrometer, a time-stretch spectrometer, a thermal infrared spectrometer, an ultraviolet photoelectron spectrometer (UPS), a video spectrometer, a vibrational circular dichroism spectrometer, and an X-ray photoelectron spectrometer (XPS).

In a ninth embodiment, the present invention provides an imaging and display system of as in the first embodiment, further comprising: a peripheral interface coupled to said computing device, said peripheral interface adapted to communicate with one or more peripherals, wherein said peripheral comprises a tracking system selected from the group consisting of: an optical tracking system, an electromagnetic tracking system, a radio frequency tracking system, a gyroscope tracking system, a video tracking system, an acoustic tracking system, and a mechanical tracking_system.

In a tenth embodiment, the present invention provides an imaging and display system as in the ninth embodiment, wherein the movement of said detector is configured to be tracked by said tracking system, such that the position of said intra-operative image captured by said detector is adjusted to maintain registration with said pre-operative image.

In an eleventh embodiment, the present invention provides an imaging and display system as in the fifth embodiment, wherein said one or more peripherals comprises a tracking system and an imaging or sensing probe, said probe capturing imaging or sensing data for composite presentation with said intra-operative image and said pre-operative image on said display.

In a twelfth embodiment, the present invention provides an imaging and display system as in the eleventh embodiment, wherein said probe comprises an in-vivo microscopy probe.

In a thirteenth embodiment the present invention provides an imaging and display system as in the eleventh embodiment, wherein the movement of said in-vivo microscopy probe is configured to be tracked by said tracking system, such that the position of said probe is presented on said display.

In a fourteenth embodiment, the present invention provides the imaging and display system as in the first embodiment, wherein said display comprises a stereoscopic display.

In a fifteenth embodiment, the present invention provides an imaging and display system as in the first embodiment, wherein said detector comprises a stereoscopic detector.

In a sixteenth embodiment, the present invention provides an imaging and display system as in the first embodiment, wherein said display presents a plurality of different imaging or sensing data in a picture-in-picture format.

In a seventeenth embodiment, the present invention provides an imaging and display system as in the first embodiment, wherein said detector is configured to detect one or more types of said intra-operative images selected from the group consisting of: a fluorescence image, a reflectance image, a color image, a light absorption image, a light scattering image, an oxygenation saturation image, a polarization image, a thermal image, an infrared image, a hyperspectral image, a light field image, a fluorescence lifetime image, a bioluminescence image, a Cerenkov image, a phosphorescence hyperspectral image, a spectroscopic image, a chemiluminescence image and a scintillation image.

In an eighteenth embodiment, the present invention provides an imaging and display system as in the first embodiment, wherein said pre-operative images comprise tomographic images.

In a nineteenth embodiment, the present invention provides an imaging and display system as in the first embodiment, wherein said pre-operative images comprise 3D models processed from pre-operative tomographic data.

In a twentieth embodiment, the present invention provides an imaging and display system as in the first embodiment, wherein said computing unit is configured to perform the steps comprising: computing a transformation matrices between a pre-operative image space, an intra-operative object/patient space and an intra-operative image space; and co-registering said pre-operative image space, said intra-operative image space and said intra-operative object/patient space.

In a twenty-first embodiment, the present invention provides an imaging and display system as in the first embodiment, wherein said computing unit is configured to perform the steps comprising: computing a transformation matrices between a pre-operative image space, an intra-operative object/patient space, an intra-operative image space and a peripheral image space; and co-registering said pre-operative image spaces, said intra-operative image space, said peripheral image space, and said intra-operative object/patient space.

In a twenty-second embodiment, the present invention provides an imaging and display system as in the first embodiment, further comprising: a light source for illuminating said target.

In a twenty-third embodiment, the present invention provides an imaging and display system as in the twenty-second embodiment, wherein said light source comprises one or more white light-emitting diodes and one or more band-rejection optical filters, wherein the frequencies of light emitted by said light source that overlaps with a fluorescence emission from said target is blocked by said band-rejection optical filters.

In a twenty-fourth embodiment, the present invention provides an imaging and display system as in the first embodiment, further comprising: a light source for illuminating said target, wherein said light source comprises one or more projectors and one or more spectral filters.

In a twenty-fifth embodiment, the present invention provides an imaging and display system as in the first embodiment, further comprising: a light source wherein said light source comprise a pulsed illumination device, or may utilize frequency modulation or pulse-duration modulation.

In a twenty-sixth embodiment, the present invention provides an imaging and display system as in the first embodiment, further comprising: a light source, wherein said light source emits an illumination beam that is provides an adjustable level of light frequencies that overlap with an emission spectra of said target.

In a twenty-seventh embodiment, the present invention provides an imaging and display system as in the first embodiment, further comprising: a peripheral interface coupled to said computing unit, said peripheral interface adapted to communicate with one or more peripherals, wherein said peripherals comprise one or more tracking systems, wherein said tracking systems comprise LEDs and spectral filters.

In a twenty-eighth embodiment, the present invention provides an imaging and display system as in the first embodiment, further comprising: a peripheral interface coupled to said computing device, said peripheral interface adapted to communicate with one or more peripherals, wherein said peripherals comprise one or more tracking systems, wherein said tracking systems comprise software that enable topology sampling using a tracked handheld imaging probe or a tracked handheld sensing probe.

In a twenty-ninth embodiment, the present invention provides an imaging and display system as in the first embodiment, wherein said computing unit stores educational or medical training contents.

In a thirtieth embodiment, the present invention provides an imaging and display system for guiding medical interventions comprising: a plurality of goggles, each including: a stereoscopic display for viewing by the eyes of one wearing the goggle, a stereoscopic detector coupled to said stereoscopic display, said detector having a field of view and projecting an image within that field of view onto said display, and a communication interface linking each of said plurality of goggles to communicate with each other.

BRIEF DESCRIPTION OF THE DRAWINGS

These and other features and advantages of the present invention will become better understood with regard to the following description, appended claims, and accompanying drawings wherein:

DETAILED DESCRIPTION OF THE INVENTION

Figure 1:
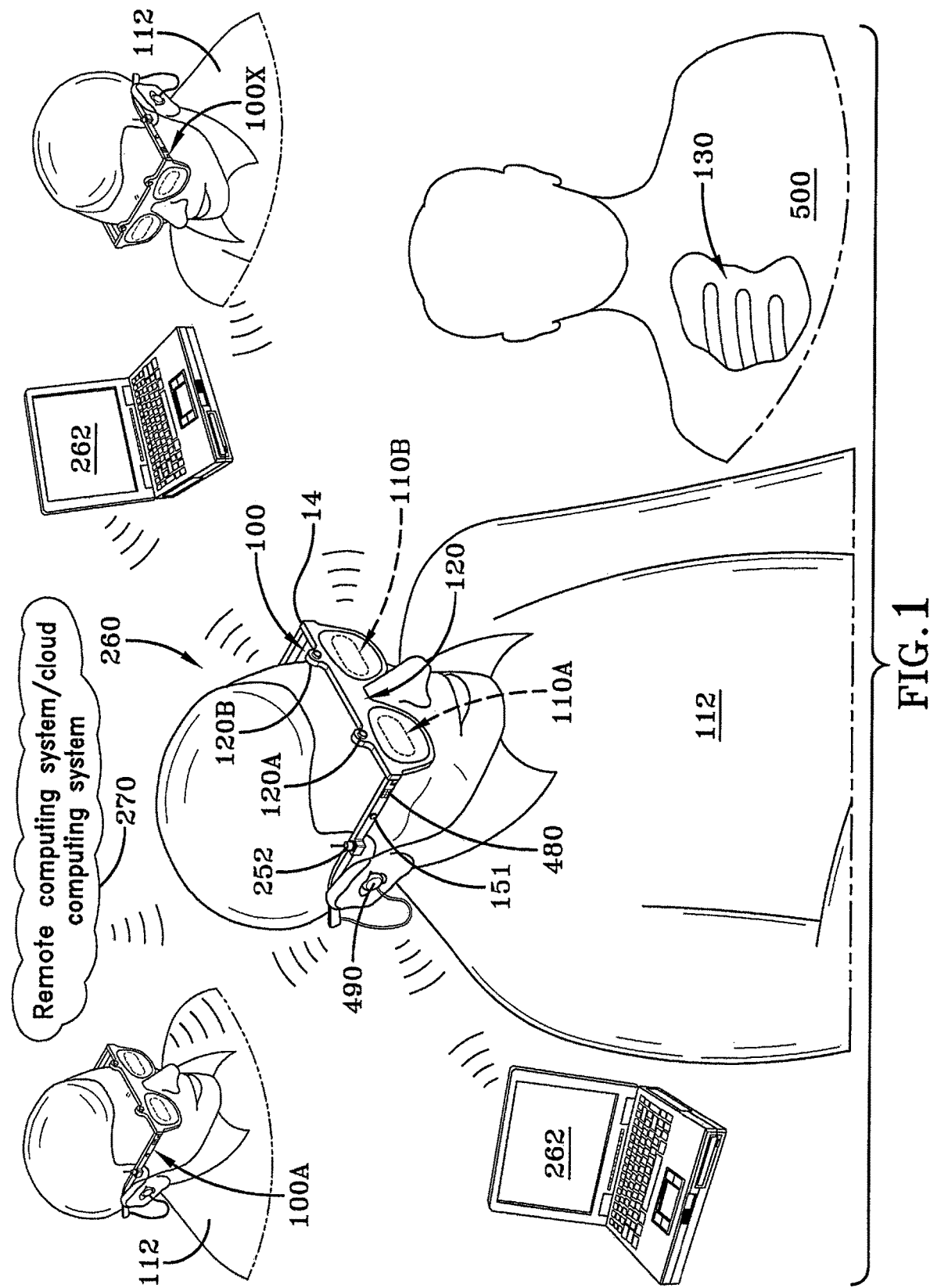
FIG. 1 is a perspective view of an imaging and display system for guiding medical interventions in accordance with the concepts of the present invention.

An imaging and display system for guiding medical interventions is generally referred to by reference numeral 100, as shown in FIG. 1 of the drawings. The system 100, shown in detail in FIG. 2, includes a display 110, which may comprise any suitable display, such as a wearable display that is configured for being attached to and worn by a user 112. For example, the wearable display 110 may be included as part of a goggle-type wearable device 114 shown in FIG. 1, which comprises a wearable goggle or eye-piece frame that carries the display 110.

In one aspect, the display 110 may comprise a single display element suitable for providing a single, continuous display that provides a single display surface that encompasses the totality of the user's field of view, or portion thereof. Alternatively, multiple separate display elements, may be used by the display, such as a dedicated right and a dedicated left display, such as in the case of a stereoscopic display, which provides an independent displays, designated as 110A and 110B, as shown in FIG. 1, to provide the field of view of each user's eye.

Furthermore, the display 110 may comprise an LCD (liquid crystal display) display, an OLED (organic light emitting diode) display, a projection display; a head-mounted display (HMD), a head-mounted projection display (HMPD), an optical-see through display, a switchable optical see-through display, a selective occlusion see-through head-mounted display, and a video see-through display. Furthermore, the display 110 may comprise an augmented reality window, augmented monitors, a projection on the patient/projective head-mounted display, selective occlusion see-through head-mounted display, and retinal scanning display. In another aspect, the display 110 may be configured to display any static or moving image. The display 110 may also comprise a picture-in-picture (PIP) display that can display images from multiple independent image sources simultaneously. In one example, the in vivo microscopy image and intraoperative fluorescence image are displayed in a picture-in-picture fashion. In another example, the ultrasound image and intraoperative fluorescence image are displayed in a picture-in-picture fashion. In another example, preoperative tomographic images and intraoperative color images can also be displayed in a picture-in-picture fashion.

In one aspect, the display 110 may comprise a stereoscopic display capable of displaying stereoscopic images with depth perception. In another aspect, the display can be other type of 3D display capable of displaying 3-dimensional images with depth perception. In still another embodiment, the display 110 may be configured to provide overlaid images of various opacity/transparency to allow simultaneous viewing of multiple images on the display 110 at one time. In yet another embodiment, the display 110 may be at least partially transparent to allow a user to view the image being displayed, while allowing the user to simultaneously see through the display 110 to also view the user's surrounding environment with natural vision at the same time.

Coupled to the display is a detector 120, which is used to acquire intra-operative images, which will be discussed in detail below. It should be appreciated that the intra-operative images acquired by the detector 120 may be acquired and displayed at the display 110 in real-time or near real-time. Specifically, the detector 120 is configured to capture any desired static or moving image data from a target of interest (TOI) 130, which may comprise any desired object, such as a wound that is being treated in a patient 500, as shown in FIG. 1. That is, the detector 120 includes a field of view that captures image data of the target of interest 130 that is within the field of view. It should also be appreciated that the detector 120 may be used in conjunction with any suitable optical lens or optical assembly to provide any desired field of view, working distance, resolution and zoom level. In one aspect, the detector 120 may comprise a camera, such as a charge-coupled device (CCD), a complementary metal-oxide semiconductor device (CMOS), one or more photomultiplier tubes (PMT), one or more avalanche photodiodes (APD), photodiodes, and a thermographic camera, such as an infrared detector. In addition, the detector 120 may comprise one or more image intensifier tubes, a microchannel plate image intensifier, and a thin-film image intensifier.

In some embodiments, the detector is a single detector 120. In one embodiment, the detector 120 may comprise a stereoscopic detector, which includes multiple imaging sensors or cameras designated respectively as 120A and 120B, as shown in FIGS. 1, which take stereoscopic images that can be displayed at stereoscopic display 110 with depth perception.

Figure 3A:
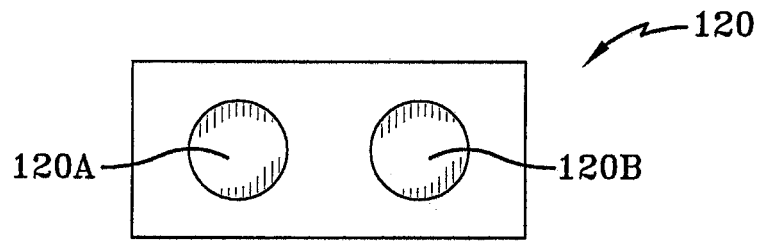
FIG. 3A is schematic diagram showing the components of a detector provided by the imaging and display system when configured with stereoscopic imaging sensors in accordance with the concepts of the present invention.

In another embodiment, the detector 120 may comprise a stereoscopic detector, which includes multiple imaging sensors or cameras designated respectively as 120A and 120B, as shown in FIGS. 1 and 3A, whereby each individual camera 120A-B includes multiple individual sensor elements. For example, the cameras 120A-B may be each configured with a first and second sensor element, whereby the first sensor element provides for full-color imaging and the second sensor element provides selective or switchable florescence imaging. Further discussion of various configurations of the various sensor elements that form the cameras 120A-B will be discussed in detail below.

The detector 120 may be configured to perform one or more imaging modes, including but not limited to fluorescence imaging, thermal imaging, oxygen saturation imaging, hyperspectral imaging, photo acoustic imaging, interference imaging, optical coherence tomography imaging diffusing optical tomography imaging, ultrasound imaging, nuclear imaging (PET, SPECT, CT, gamma, X-ray), Cerenkov imaging, and the like. In addition, the detector 120 may also be configured to perform real-time/offline imaging, including absorption, scattering, oxygenation saturation imaging, fluorescence imaging, fluorescence lifetime imaging, hyperspectral imaging, polarization imaging, IR thermal imaging, bioluminescence imaging, phosphorescence imaging, chemilluminescence imaging, scintillation imaging, and the like.

The display 110 and the detector 120 are coupled to a computing unit 200. The computing unit 200 may be part of a wearable version of the system 100 or might alternatively be an external computing unit 200. The computing unit 200 includes the necessary hardware, software or combination of both to carry out the various functions to be discussed. In one aspect, the computing unit 200 may comprise a microprocessor or may comprise any other portable or standalone computing device, such as a smartphone, capable of communicating with the various components of the system 100. It should also be appreciated that the computing system 200 may also include a memory module to store various data to be discussed. In addition, the computing unit 200 is configured, whereby the image data acquired by the detector 120 may be processed and transmitted by the computing unit 200 in various manners to be discussed. It should also be appreciated that the computing unit 200 may include a local or remotely accessible memory or storage unit, which allows the computing unit to store and/or acquire various programs, algorithms, databases, and decision support systems that enable a variety of functions to be discussed, which may be based on the image data collected by the detector 120. In one aspect the system 100 may be powered by any suitable power source, such as a portable power source comprising one or more batteries or a plug-in type power source for connection to a standard electrical wall outlet.

In one aspect, the local or remote memory unit may store various pre-operative image data, such as tomographic image data from Mills and CT scans, which will be discussed in detail below.

In another aspect, the computing unit may perform image segmentation and generate a 3D model based on the preoperative imaging data. The 3D model may be stored in the local or remote memory unit.

In one aspect, the pre-operative image data, such as Mill (magnetic resonance imaging) data for example, is segmented and processed into a 3-dimensional model having a plurality of 3D surfaces. It should be appreciated that any suitable segmentation process may be used, including: either automatic, manual or semi-automatic segmentation processes. In addition, segmentation can also be based on thresholding methods, clustering methods, compression-based methods, histogram-based methods, edge detection methods, region-growing methods, split-and-merge methods, partial differential equation-based methods, parametric methods, level set methods, fast marching methods, graph portioning methods, watershed transformation methods, model based segmentation methods, multi-scale segmentation methods, trainable segmentation methods, and any combination thereof.

In operative communication with the field of view of the detector 120 is a filter 150. Accordingly, the filter 150 serves to process the light that travels from the target of interest (TOI) 130 before the light is received at the detector 120 in the form of image data, such as image data for use during intra-operative imaging. As such, the filter 150 is configured to use any suitable technique to process the image data collected by the field of view of the detector 120. In one aspect, the system 100 may be configured so that filter 150 is brought into or out of operative communication with the detector 120, so that the image data collected by the field of view of the detector 120 is selectively filtered or unfiltered. In one aspect, the selective filtering performed by the filter 150 may be carried out by any suitable mechanism, such as an electro-mechanical mechanism, which is initiated by any suitable switching device 151, such as a mechanical switch, or voice command to move the filter 150. Accordingly, when the switchable filter 150 is in operative communication with the detector 120 the system 100 is placed into a first mode for detecting TOIs 130 that emit frequencies within a spectrum of frequencies defined by the physical parameters of the filter, such as the spectrum of frequencies emitted during the fluorescence of materials. Alternatively, when the filter 150 is not in operative communication with the detector 120, the system 100 is placed into a second mode for detecting TOIs 130 within another frequency spectrum, such as the spectrum of frequencies for reflectance off the TOIs.

It should be appreciated that the filter 150 may comprise a filter wheel having different discrete filter of different filtering properties, which can be selectively rotated into operative alignment with the detector 120. In addition, the filter 150 may comprise a long-pass filter, a band-pass filter, a tunable filter, a switchable filter, and the like.

In another aspect, the filter 150 may comprise an 830 nm band-pass filter.

In other embodiments, the filter 150 may be replaced by a polarizer 152 and operate in the same manner with respect to the detector 120 as discussed above with regard to the filter 150. Furthermore, in other embodiments the polarizer 152 may be simultaneously used together with the filter 150, whereby the field of view of the detector 120 is processed by both the polarizer 152 and by the filter 150 prior to detection by the detector 120. It should also be appreciated that the polarizer 152 may comprise a switchable polarizer that operates in the same manner as the switchable filter 150, or may comprise a tunable polarizer.

Accordingly, the ability to selectively filter or selectively polarize the field of view being detected by the detector 120 embodies a "convertible" system, whereby when the detector 120 is unfiltered, it is in a first mode, which is capable of a first imaging state, such as reflectance imaging; and when the detector is placed or "converted" into its second mode, it is capable of a second imaging state, whereby it is capable of fluorescence imaging for example.

Figure 3B:
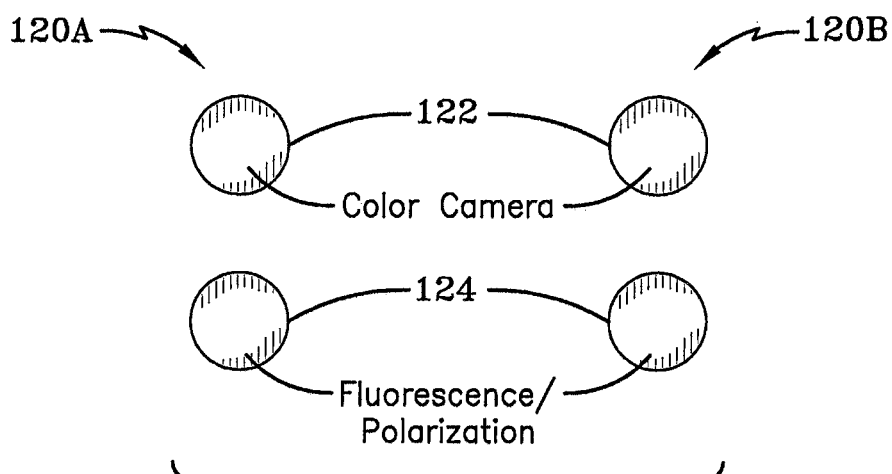
FIG. 3B is a schematic diagram of an alternative configuration of the detector, whereby multiple sensor element types are used for each of the stereoscopic imaging sensors shown in FIG. 3A in accordance with the concepts of the present invention.
Figure 3C:
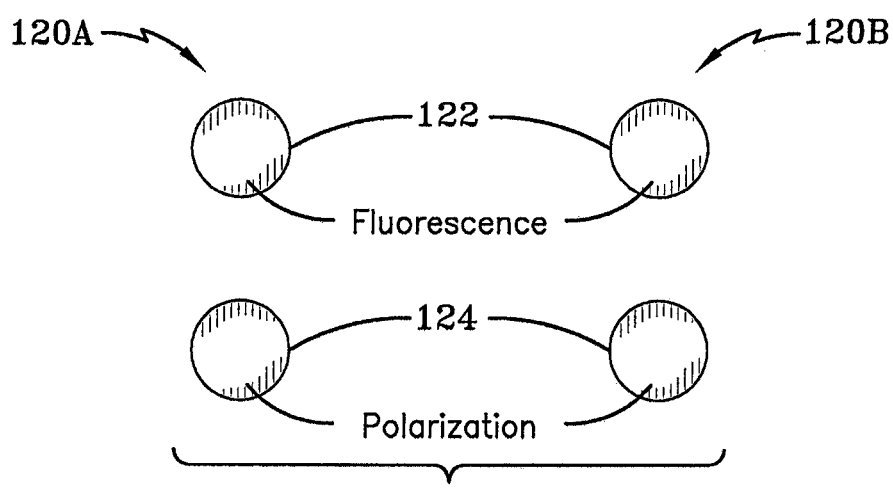
FIG. 3C is a schematic diagram of another configuration of the detector, whereby multiple sensor element types are used for each of the stereoscopic imaging sensors shown in FIG. 3A in accordance with the concepts of the present invention.
Figure 3D:
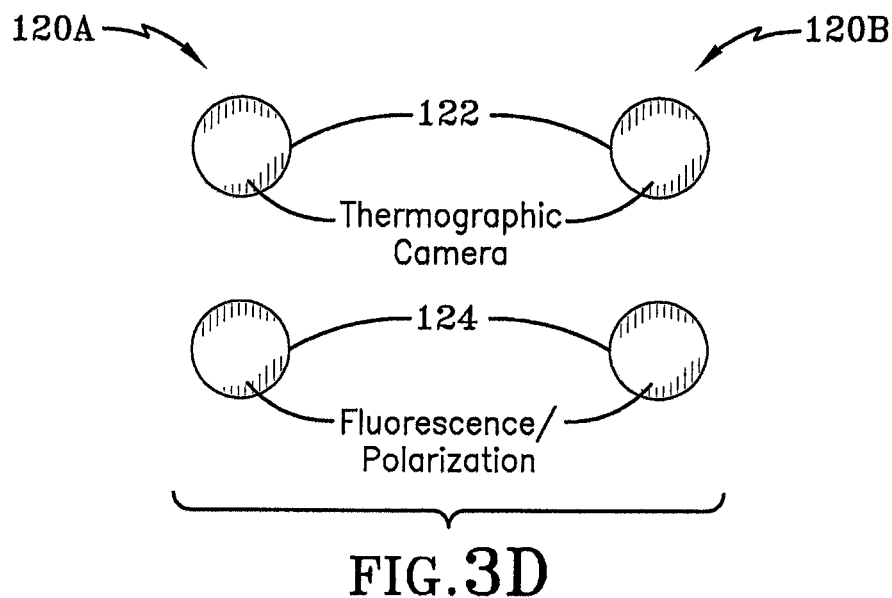
FIG. 3D is a schematic diagram of a further configuration of the detector, whereby multiple sensor element types are used for each of the stereoscopic imaging sensors shown in FIG. 3A in accordance with the concepts of the present invention.
Figure 3E:
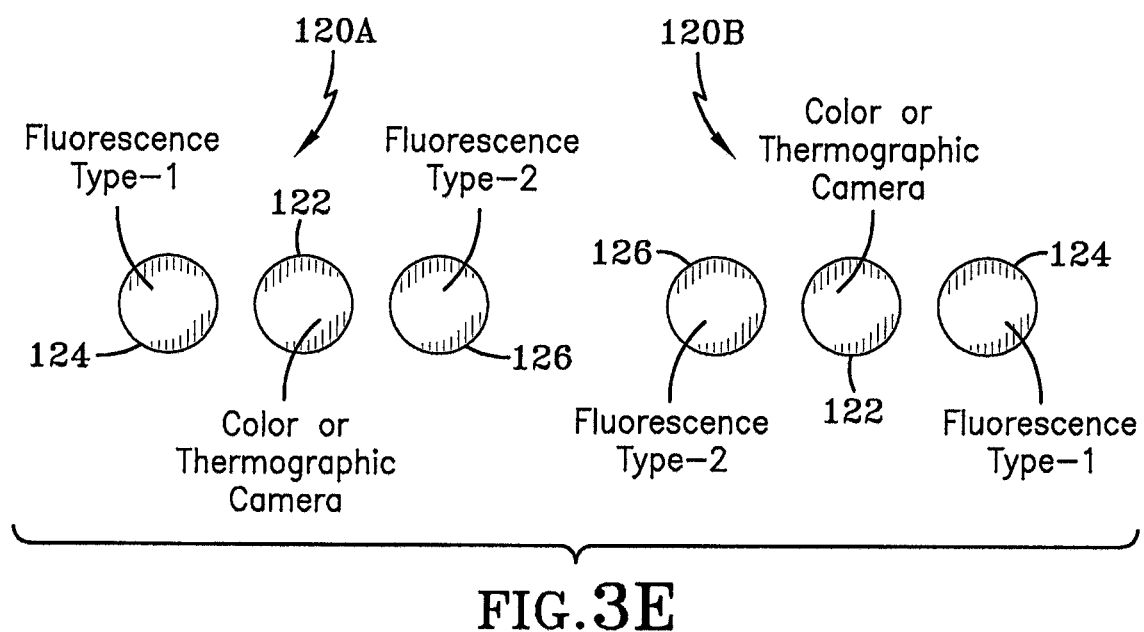
FIG. 3E is a schematic diagram of another configuration of the detector, whereby multiple sensor element types are used for each of the stereoscopic imaging sensors used for each of the stereoscopic imaging sensors shown in FIG. 3A in accordance with the concepts of the present invention.

Furthermore, using the combination of the cameras 120A-B each having multiple imaging elements together with the selective use of the filter 150 or polarizer 152 allows for a variety of modes of operation. For example, in FIGS. 3B-D the detector 120 is configured such that each camera 120A and 120B has two sensor elements 122 and 124, whereby the first sensor element 122 is used for a first imaging mode (or a convertible detection mode that is switchable between among two or more imaging modes) and the second sensor element 124 is used for a second convertible imaging mode, which provides selective imaging among two or more imaging modes. Thus, in FIG. 3B, sensor element 122 of cameras 120A-B are operate in a color imaging mode, while sensor elements 124 of cameras 120A-B operate in a convertible filter mode, that can be switched between florescence imaging with different spectral frequencies; or between polarization imaging with different polarization states. In addition, FIG. 3C shows that the sensor element 122 of cameras 120A-B is switchable between different modes of fluorescence imaging, while sensor element 124 of cameras 120A-B are switchable between different modes of polarization imaging. Furthermore, FIG. 3D shows that the sensor element 122 of cameras 120A-B is a thermographic sensor, while sensor element 124 of cameras 120A-B are switchable between different modes of fluorescence imaging; or switchable between different modes of polarization imaging. Additionally, FIG. 3E shows the use of three sensor elements, whereby sensor element 124 of cameras 120A-B offer a first-type of fluorescence imaging modes; sensor element 122 of cameras 120A-B is offer color imaging or thermographic imaging; and the sensor element 126 of cameras 120A-B offers a second-type of fluorescence imaging modes.

Coupled to the computing system 200 is a communication interface 250, which includes a suitable antenna 252 for communicating wirelessly or via a wired connection with a communication network 260. The system 100 may communicate via the communication network 260 with other imaging and display devices 100A-X, or any other networked computer system 262, such as laptop computers, smart phones, and the like, as shown in FIG. 1. In one aspect, the communication interface 250 is embodied as a transceiver that is enabled to both transmit and receive data via the network 260. In one aspect, the communication interface 250 may be configured to communicate over the network 260 using any suitable method, including RF (radio frequency) signals, such as a low-power RF signals, a wired or wireless Ethernet communication method, a WiFi communication method, a Bluetooth communication, cellular communication (e.g. 3G, 4G, LTE, etc.) and the like. As such, the ability of multiple systems 100 to communicate with each other enables a variety of functions, which will be discussed in detail below.

The communication interface 250 also enables network and cloud computing features to be carried out by the imaging and display system 100. In one aspect, the communication interface 250 allows the system 100 to communicate with a remote storage devices on a remote network or a remote cloud computing system, generally represented by the numeral 270, as shown in FIG. 1 to allow access centralized data storage, conduct further computing analysis, access to other software applications, and to enable record storage. For example, the system 100 may acquire pre-operative images from the remote network 270.

Also coupled to the computing device 200 is a peripheral interface 300. The peripheral interface may comprise a wired or wireless interface that allows for the addition of one or more peripherals 350 to be selectively added to the imaging and detection system 100. The peripherals may comprise one or more sensors and detectors. For example, such add-on peripheral 350 may include a vital sign sensor module, that may monitor one or more of: temperature, blood pressure, pulse, respiratory rate, ECG, EEG, pulse oximetry, blood glucose, and the like. The peripheral 350 may also include an ultrasound module, a spectroscopy module (e.g. Raman spectroscopy, absorption spectroscopy, and reflectance spectroscopy), a GPS (global positioning system) module, a microscope module (e.g. a handheld microscope, a fiber-based in-vivo microscope, and a traditional microscope), and a non-microscopic imaging module (hyperspectral imaging, photoacoustic imaging, optical coherence imaging).

In another aspect, the peripheral 350 may comprise a probe instrument, such as a hand-held probe used to acquire or sense any in-vivo target of interest 130. As such, the hand-held probe may be used for any desired type of microscopy, such as in-vivo microscopy. The probe may utilize various detection methods, such as color microscopy, reflectance microscopy, fluorescence microscopy, oxygen-saturation microscopy, polarization microscopy, infrared microscopy, interference microscopy, phase contrast microscopy, differential interference contrast microscopy, hyperspectral microscopy, total internal reflection fluorescence microscopy, confocal microscopy, non-linear microscopy, 2-photon microscopy, second-harmonic generation microscopy, super-resolution microscopy, photoacoustic microscopy, structured light microscopy, 4Pi microscopy, stimulated emission depletion microscopy, stochastic optical reconstruction microscopy, ultrasound microscopy, and/or a combination of the aforementioned, and the like.

In another aspect, the handheld probe used as the peripheral 350 may be a imaging device that has not reached microscopic resolution yet. In some embodiments, the non-microscopic imaging method is selected from one or more of the following: reflectance imaging, fluorescence imaging, Cerenkov imaging, polarization imaging, ultrasound imaging, radiometric imaging, oxygen saturation imaging, optical coherence tomography, infrared imaging, thermal imaging, photoacoustic imaging, spectroscopic imaging, hyper-spectral imaging, fluoroscopy, gamma imaging, and X-ray computed tomography. The physical form of the handheld probe may comprise an endoscope, a laparoscope, a bronchoscope, an angioscope, and a catheter for angiography.

In still another example, the handheld probe may be a non-imaging device or a sensing device, such as a fiber-based spectrophotometer. In addition, different spectroscopies may be realized by the peripherals 350, such as various optical spectroscopies, absorption spectroscopy, fluorescence spectroscopy, Raman spectroscopy, Coherent anti-Stokes Raman spectroscopy (CARS), surface-enhanced Raman spectroscopy, Fourier transform spectroscopy, Fourier transform infrared spectroscopy (FTIR), multiplex or frequency-modulated spectroscopy, X-ray spectroscopy, attenuated total reflectance spectroscopy, electron paramagnetic spectroscopy, electron spectroscopy, gamma-ray spectroscopy, acoustic resonance spectroscopy, auger spectroscopy, cavity ring down spectroscopy, circular dichroism spectroscopy, cold vapour atomic fluorescence spectroscopy, correlation spectroscopy, deep-level transient spectroscopy, dual polarization interferometry, EPR spectroscopy, force spectroscopy, Hadron spectroscopy, Baryon spectroscopy, meson spectroscopy, Inelastic electron tunneling spectroscopy (LETS), laser-induced breakdown spectroscopy (LIBS), mass spectroscopy, Mossbauer spectroscopy, neutron spin echo spectroscopy, photoacoustic spectroscopy, photoemission spectroscopy, photothermal spectroscopy, pump-probe spectroscopy, Raman optical activity spectroscopy, saturated spectroscopy, scanning tunneling spectroscopy, spectrophotometry, time-resolved spectroscopy, time-stretch Spectroscopy, thermal infrared spectroscopy, ultraviolet photoelectron spectroscopy (UPS), video spectroscopy, vibrational circular dichroism spectroscopy, X-ray photoelectron spectroscopy (XPS), or a combination of the aforementioned.

Tracking and Registration of Multiple Images for Display

In some embodiments, the system 100 includes a tracking module, which can be considered another peripheral 350, and includes software suitable for tracking the spatial location of the patient, location of the detector 120 (or 120A, 120B) and the location of peripherals 350, such as imaging cameras and probes, and registering these locations relative to the image(s) of the detector 120 or detectors 120A, 120B (in stereoscopic modalities). Reference to detector 120 herein will also be understood to be equally applicable to the stereoscopic modalities of those systems 100 employing detectors 120A and 120B. Furthermore, through tracking the position of the patient and the position of the detector 120

(or 120A, 120B), the preoperative images (such as CT, MIII, SPECT, PET images) can be registered to the image(s) of the detector 120 or detectors 120A, 120B (in stereoscopic modalities). Thus, the corresponding imaging and sensing information obtained from the peripheral 350, and the preoperative images, can be correlated with the field of view imaged by the detector 120 of the imaging and display system 100. That is, the system 100 may be programmed to utilize tracking and registration techniques to allow for the overlay of multiple images acquired directly by the detector 120 of the system 100, with preoperative images, and with those images acquired by peripheral image detectors, such as hand-held microscopy probes, or the like. In some embodiments, the tracking module can also track and register the location of other non-peripheral elements, such as the tools being employed by military or medical personnel. For example, the location of scalpels or clamps or stents or other elements of a medical operation could be tracked and registered with the images. It should be appreciated that the software enabling such tracking and registration features may be provided from a remote computer system to the system 100 via the network 260 or stored on any peripheral attached to the peripheral interface 300. Specifically, tracking techniques utilized by the system 100 obtain the position of a patient to be treated by the system 100, the system 100 itself comprising the wearable display 114, and the handheld imaging peripheral 350 coupled to the peripheral interface 300.

It should also be appreciated that the peripheral module 350 may include a tracking module, which allows the spatial location of the detector 120, and spatial location of plug-in modules within the peripheral 350, such as imaging cameras and probes. Thus, the corresponding imaging and sensing information obtained from the peripheral 350 can be correlated with the field of view imaged by the detector 120 of the imaging and display system 100. That is, the system 100 may be programmed to utilize tracking and registration techniques to allow for the overlay of multiple images acquired directly by the detector 120 of the system 100 with those images acquired preoperatively (such as CR, MRI, SPECT, PET, X-ray, Gamma imaging, etc). Alternatively, the system 100 may be programmed to utilize image tracking and registration techniques to allow for the overlay of multiple images acquired directly by the detector 120 of the system 100 with those 3D models constructed based on data acquired preoperatively (such as CR, MRI, SPECT, PET, X-ray, Gamma imaging, etc). Furthermore, the system 100 may be programmed to utilize image tracking and registration techniques to allow for the overlay of multiple images acquired directly by the detector 120 of the system 100 with those images acquired (i.e. imaged/sensed) by peripheral image detectors, such as hand-held in-vivo microscopy probes 350, or the like. Similarly, multiple images acquired directly by the detector 120, preoperative images or 3D models, images acquired (i.e. imaged/sensed) by peripheral image detectors 350 can be overlaid and registered together. It should be appreciated that peripheral sensing detectors 350 data may also be registered with multiple images acquired directly by the detector 120, preoperative images or 3D models. It should be further appreciated that the picture-in-picture display and overlaid display can be used in conjunction with each other, in a hybrid mode. It should be appreciated that the software enabling such tracking and registration features may be provided from a remote computer system, such as remote system 270, to the system 100 via the communication network 260 or stored on any peripheral attached to the peripheral interface 300. Specifically, tracking techniques utilized by the system 100 obtain the position of each of the following: the position of the patient to be treated using the system 100, the position of the system 100 itself comprising the wearable system including the display 110 and detector 120, and the position of the handheld imaging/sensing peripheral 350, such as in-vivo probe, coupled to the peripheral interface 300.

Furthermore, the tracking functions may be carried out using optical tracking or magnetic tracking devices that are employed as a peripheral 350. If optical tracking is used, active markers such as LEDs may be attached to detector 120, the imaging or sensing probe employed as another peripheral 350 and the patients, to locate their locations, respectively. NDI Optotrak Certus system is an example of optical tracking systems that may be used for this embodiment. Commercially available optical tracking systems may consist of CCD cameras and sequentially illuminated infrared (IR) LEDs, and can be easily integrated as a peripheral 350, into the wearable imaging and display device 100. Alternatively, one may use a videometric system to estimate patient pose and instrument orientation by identification of passive markers in video-image sequences.

In one aspect, optical tracking using NDI Optotrak Certus may incorporated as a peripheral 350 to provide tracking, whereby light emitting diodes (LED) are attached to the wearable device 100 that carries the detector 120, and imaging module as another peripheral 350, such as ultrasound and hand-held microscopy probes and patients. As such, the LEDs attached to the detector 120, hand-held probe 350, and patients are tracked by the NDI Optotrak Certus system.

In another embodiment, a novel infrared optical tracking method may be utilized by the system 100. As such, the wavelength of the optical emitters for tracking purposes (such as LEDs) attached to the patient, wearable imaging and display system 100, and intraoperative imaging peripheral 350, may be different wavelengths from the wavelengths detected by the detector 120, and imaging peripheral 350. Methods, such as spectral filtering may be used to facilitate the separation of wavelengths between the optical emitter from the tracking system and the detection of the detector 120, and imaging peripheral 350. Frequency modulation may also be used to separate the signal from the tracking optical emitters from the signal-of-interest of the detector 120, and imaging peripheral 350.

In another example, gyroscopic tracking in combination with video tracking may be performed using the module 350.

If electromagnetic tracking is used, the peripheral 350 may incorporate small coils or similar electromagnetic field sensors and multiple position measurement devices. The electromagnetic field sensors may be attached to detector 120, the imaging or sensing probe employed as another peripheral 350 and the patients, to locate their locations, respectively.

Alternatively, the tracking functions may be carried out using fiducial markers, such as LEDs, attached to the patient to be treated, the wearable imaging and display device 100, and the imaging peripheral 350. With the position obtained using the tracking techniques described, enabled by tracking systems as a peripheral 350, registration, or alignment, of the different images obtained by the imaging and display device 100 and the handheld imaging peripheral 350 is performed by using transformation matrices between preoperative imaging space, intraoperative object space (i.e patient space), intraoperative imaging space (device 100 imaging space), and the handheld peripheral imaging/sensing probe 350 space (i.e. peripheral imaging probe space) can be calculated. Specifically, the image registration process is carried out such that preoperative imaging space can be registered to intraoperative object space (patient space); intraoperative imaging space (device 100 imaging space) can be registered to intraoperative object space (patient space); and handheld device imaging space (peripheral 350 eg. Ultrasound, fiber microscope, etc.) can be registered to intraoperative object space (patient space). As a result, the co-registered intra-operative images obtained from the detector 120 of the wearable system 100 and the in-vivo images acquire from the in-vivo probe peripheral 350, and pre-operative tomography images can be displayed in the wearable display in an overlaid and aligned manner.

Thus, in some embodiments, the tracking functions may be carried out using fiducial markers, such as LEDs, attached to (a) the patient to be treated or an object to be acted upon or observed (in the instance of non-medical applications), (b) the wearable imaging and display device 100, and (c) the peripheral 350. Through the use of fiducial markers, images of the same subject produced with multiple distinct imaging systems—for example, the detector 120 as a first imaging system, and any desired peripheral 350 that generates a second image as the second imaging system—may be correlated by placing fiducial markers in the area imaged by both systems. Appropriate software correlates the two images, and in the case of the present invention, permits viewing of the two (or more) images overlaid together or in a picture-in-picture format.

Figure 5:
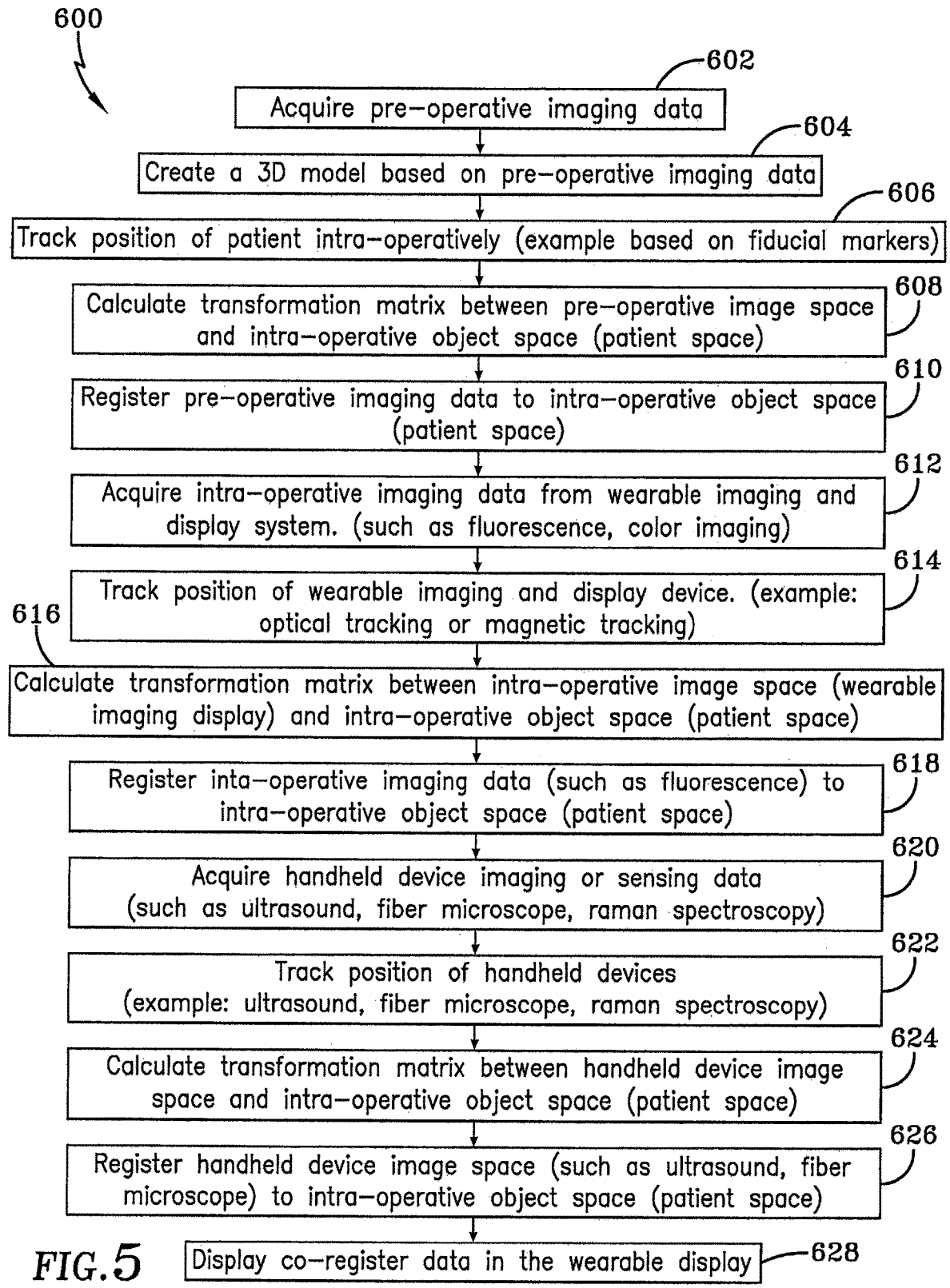
FIG. 5 is a flow diagram showing the operational steps for a tracking and registration process in accordance with the concepts of the present invention.

It should be appreciated that during the tracking and registration processes the computing unit 200 carry out computations and execute software to enable the accurate tracking and registration. In one aspect, the complete registration processes are represented by a flowchart is shown in FIG. 5 designated by number 600. Generally, the process 600 obtains the position of the patient 500, the wearable imaging and display system 100, and the handheld probe 350. Initially, at step 602, the system 100 acquires pre-operative imaging data. Next, at step 604 a 3D model is created based on the pre-operative imaging data. At step 606 the position of the patient is tracked intra-operatively using any suitable technique, such as fiducial markers for example. At step 608 a transformation matrix is calculated between the pre-operative image space and the intra-operative object space (i.e. patient space). Continuing, the pre-operative image data is registered to the intra-operative object space (i.e. patient space), as indicated at step 610. At step 612, the intra-operative imaging data is acquired from the wearable imaging and display system 100, such as fluorescence or color imaging for example. Continuing to step 614, the position of the wearable imaging and display system 100 is obtained, using any suitable technique, such as optical tracking or magnetic tracking). At step 616, calculate the transformation matrix between the intra-operative imaging space (i.e. wearable imaging and display system) and the intraoperative object space (patient space). Next, at step 618 register the intra-operative imaging space (such as fluorescence image data) to the intra-operative object space (i.e. patient space). At step 620, the process 600 acquires handheld device imaging or sensing data, such as ultra-sound fiber microscope, and Raman spectroscopy for example. Next, at step 622 the position of the hand-held probe 350, such as an ultrasound fiber, a microscope, and Raman spectroscopy probe is tracked. At step 624 a transformation matrix is calculated between the hand-held imaging/sensing probe 350 image space and the intra-operative object space (i.e. patient space). Next, at step 626, the hand-held device image space (i.e. ultrasound or microscope) is registered to the intra-operative object space (i.e. patient space), as indicated at step 626. Finally, at step 628 the co-registered image data is presented on the display 110 of wearable imaging and display unit 100.

In another aspect, the process 600 may be configured, such that the tracking and registration process is performed without the image data acquired from the hand-held probe 350. As a result, the process 600 only uses the intra-operative image data acquired by the imaging and display system 100 (i.e. goggle system) and the pre-operative surgical navigation image data. In such a case, only steps 602-618 and step 628 of the process 600 are required to be performed.

In yet another aspect, the process 600 may also be configured, such that the tracking and registration process is performed without the pre-operative surgical navigation image data. As a result, the process 600 only uses the intra-operative image data acquired by the imaging and display system 100 (i.e. goggle system) and the image data acquired by the hand-held probe 350. In such a case, only steps 612-626 and step 628 are performed.

It should also be appreciated that in addition to the tracking techniques described above, other tracking techniques may be used, such as radio frequency tracking, gyroscope tracking, video tracking (pattern recognition), acoustic tracking, mechanical tracking, and/or a combination thereof. In addition, the tracking method employed by the module 350 may utilize rigid body, flexible body or digitizer methods.

It should also be appreciated that in addition to the registration techniques discussed above, other registration techniques may be used, such as point-based registration, surface-based registration, and/or a combination thereof. The registration may comprise either intensity-based or feature-based registration. The transformation models used may comprise linear transformation, or non-rigid/elastic transformation. Spatial or frequency domain methods may be used, as well as automatic or interactive methods.

To sample the topology of the object space in the field of view (or the target of interest), digitizers (such as the device from NDI) may be used to sample the points in object space. Alternatively, topology acquisition systems, such as a 3D scanner may be used to capture the 3D topology, which may facilitate image registration.

The handheld probe employed as a peripheral module 350 may serve dual purposes: serving as stylus/digitizer for sampling topology; and serving as imaging or sensing probe. Specifically, the handheld probe may have optical emitters such as LEDs attached to it, which will allow location of the tip of the handheld probe with the help of the optical tracking system; Alternatively, the position of the tip can be obtained by tracking the electromagnetic sensors attached to the handheld probe using a magnetic tracking system. When the probe are swiped across different points on the surface of the organs, a 3D point cloud can be established, based on the locations of the tips of handheld probe (tip is considered to be just in contact with organs). In this way, the imaging handheld probe also enables similar functionality to sample topology as the non-imaging stylus/digitizer traditionally employed in tracking systems.

In another aspect, a tracker module employed as a peripheral module 350 may track the positions of a hand-held microscopy probe peripheral also employed as a peripheral module 350, register each image with the corresponding spatial counterpart in the preoperative image, and display in the display 110. As such, the images detected by the imaging peripherals, such as a ultrasound probe may then be overlaid with images collected, such as fluorescence images, by the detector 120 of the imaging and display system 100 for presentation on the display 110. The registration of multiple images on the display 110 may be achieved using any suitable technology, including point-based registration, surface-based registration, intensity-based, feature-based registration, and/or a combination of both. The transformation models used may comprise linear transformation, or non-rigid/elastic transformation. Spatial or frequency domain methods may be used, as well as automatic or interactive methods. For example, fiducial markers, such as LEDs, may be used to facilitate point-based registration. In another example, if surface topology or profile is available, the surface-based registration can also be used. In yet another example, the registration may also be based on pattern recognition or feature-based recognition.

Thus, by combining the functionality of the communication interface 250 and the peripheral interface 300, the system 100 is enabled to provide multiple functions. One or more peripherals of a multitude of types, including those mentioned above can be selectively coupled to the display system 100, as needed for providing the system 100 with a desired functionality. If imaging from a probe is needed in a given application, for example for in vivo imaging of a patient, a probe as a peripheral 350 can be coupled to the display system 100 at the interface 300 so that the display system 100 would then have the ability to display the image gathered from the probe. As per the tracking disclosure above, this image could be overlaid onto the image of the patient gathered by the detector 120, placing the in vivo image of the probe at the proper location on the image of the patient. Furthermore, the probe image can be overlaid onto the preoperative images, intraoperative images captured by detector 120, placing the in vivo image of the probe at the proper location on the image of the patient. In one aspect, the handheld microscopy probe can scan over a larger area over the patient sequentially. Using tracking technique discussed above, the small field of view microscopy image captured by 350 may be joined together as a montage, which is overlaid over intraoperative image captured by 120 and preoperative image.

In another aspect, a co-registration of a 4 sensor setup between color and fluorescence imaging, whereby vertical and horizontal disparities are correlated. In particular, this example describes the manner in which a 4-camera setup is used to register intraoperative color imaging to intraoperative fluorescence imaging.

In another embodiment, stereoscopic fluorescence images captured by 2 fluorescence cameras and stereoscopic color images captured by 2 color cameras can be registered together. Both sets of images were placed into side-by-side frames, and the fluorescent side-by-side frame was overlaid onto the anatomical frame by the computing module and sent to the display. For high registration accuracy, we measure the vertical distance from the center of the filtered cameras for fluorescence to the center of the unfiltered color camera as well as the horizontal baseline distance between two filtered or unfiltered cameras. From this information, a correction metric, $D_V$, was determined from the equation:

$$\frac{L_H}{L_V} = \frac{D_H}{D_V}$$

where L is the measured baseline disparity between cameras in either the horizontal (H) or vertical (V) direction, and $D_H$ is the horizontal pixel disparity between common points in the left and right fluorescent images. The points used to calculate $D_H$ were the peak fluorescent points; if more than one peak existed, one was chosen for the calculation. The fluorescent frames were then shifted up by the calculated correction metric so that, after calibration, the fluorescent image was aligned to the corresponding color image.

In addition, GPS and wireless communication between multiple imaging and display systems 100A-X can be integrated, such that information relevant to medical environments is labeled with GPS data. Thus, in one embodiment, information acquired by each system 100A-X can also be transmitted or received wirelessly, to guide medical interventions. Using telemedicine functionality of the system 100, medical operations can be performed by first responders using the system 100 under the guidance of medical practitioners that are located remotely but who are also using the system 100. It should be appreciated that the systems 100 A-X may also communicate with any other suitable computing device, such as a tablet, mobile smart phone, or the like.

In addition, the system 100 may include an illumination or light source 400 to illuminate the field of view used to image the target object of interest 130 being imaged by the detector 120. It should also be appreciated that the light source 400 is configured to deliver a light having the appropriate intensity and frequency spectrum that is compatible with the particular imaging being conducted with the detector 120, with or without the filter/polarizer 150,152. For example, it may be necessary to have a light source 400 that emits a first frequency spectrum for use in a first imaging mode, such as color reflectance imaging mode, and that emits a second frequency spectrum for use in a second imaging mode, such as a fluorescence imaging mode. In one aspect, the light source 400 may be coupled to the computing device 200 for automated control over the functions provided by the light source 400, or may be unattached from the computing device 200 and operated manually by the user of the system 100.

It should also be appreciated that the light source 400 may serve different purposes in the medical environment. Furthermore, upon conversion of the detector 120 by removal or the filter/polarizer 150,152 or by selecting the necessary filter/polarizer 150,152 the illumination of the light source 400 may be used for florescence imaging, optical imaging, photodynamic therapy, laser surgery, sterilization, and the like. It should also be appreciated that multiple light sources 400 may be used.

It should also be appreciated that the light source 400 may comprise a laser light; a light emitting diode (LED), such as a white LED; an incandescent light; a projector lamp; an arc-lamp, such as xenon, xenon mercury, or metal halide lamp; as well as coherent or in-coherent light sources.

The light source 400 may also comprise a digital (LED-based) projector, and additionally the light source may project spatial frequencies for patterned illumination. For example, a digital projector in conjunction with spectral filters may be used as the light source. In addition, the light source 400 may emit a continuous or pulsed output, and may generate light that is within any desired spectral window of electromagnetic waves.

It should also be appreciated that the light source 400 may also include a light diffuser.

Figure 2:
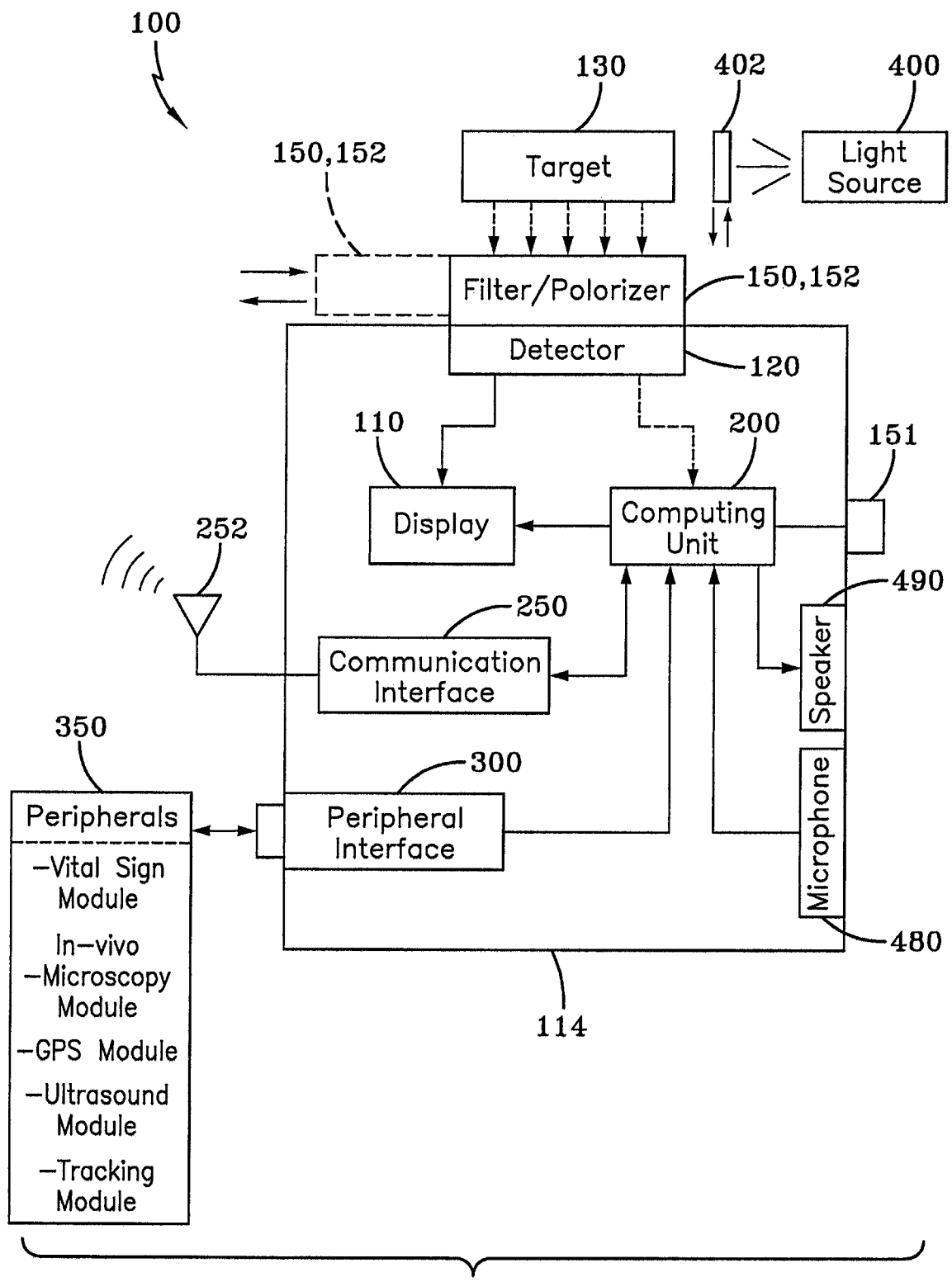
FIG. 2 is a schematic diagram showing the components of the imaging and display system in accordance with the concepts of the present invention.

Spectral Filter to Block Light Frequencies Overlapping with Fluorescence Emission Spectra In some embodiments, particularly when it is desired to observe a fluorescence emission spectra from the object being illuminated and observe through the imaging and display system 100, the light source 400 selectively shines through a spectral filter 402, as shown in FIG. 2, that blocks the wavelength of the emission spectra to be observed, such that the light source 400 does not interfere with the observance of that emitted wavelength. For example, if the object is to be observed for fluoresce at a certain wavelength, the spectral filter 402 would be chosen to block that wavelength from the light source so that the light source does not interfere with the observance of the emitted fluorescence. In some such embodiments, the light source is a white light source thus providing a broad spectrum, and the spectral filter is appropriately chosen based on the emission spectra to be observed. In some embodiments, the light source is one or more white light emitting diodes (LED). In some embodiments, the individual light sources are white light emitting diodes (LED) that are filtered by a 775 nm low-pass filter. In another embodiment, the low-pass filter may be replaced with a polarizer, or may be used in conjunction with the filter the light source shines through a spectral filter.

Figure 8:
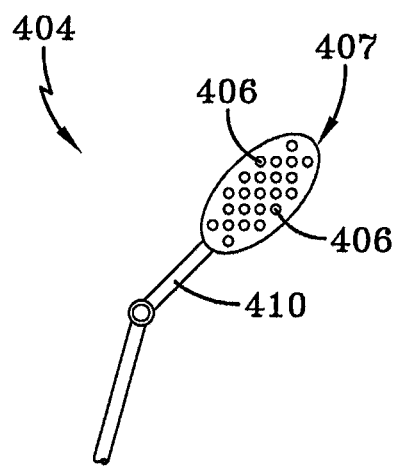
FIG. 8 is a front perspective view of a shadowless surgical light in accordance with the concepts of the present invention.
Figure 9:
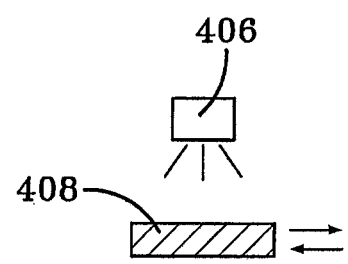
FIG. 9 is a general schematic view showing the use of a spectral filter with individual lights of the shadowless surgical light of FIG. 11 in accordance with the concepts of the present invention.

With reference to FIGS. 8 and 9, in another embodiment, the light source 400 may comprise a shadow-less light 404, which is desirable for use during surgery (i.e. a surgical light). The shadow-less light 404 includes a plurality of individual light sources 406 spaced apart in a support 407 to project light onto an object, such as patient 500, whereby a shadow cast by an intervening object and one or more of the plurality of individual light sources is negated by at least one other of the plurality of individual light sources. For example, the shadow-less light 404 can be a surgical light and a surgeon my interpose a hand and arm between the shadow-less light 404 and the patient and thus certain individual light sources would tend to cast a shadow onto the patient but for the fact that other light sources will not have the hand/arm of the surgeon interposed between the shadow-less light source and the surgeon such that those lights will negate the shadow, thus leading to shadow-less lighting. As known, the support 407 is on the end of a swing arm 410, or a goose neck or other connection providing the ability to position the light 404 as desired.

In some embodiments, particularly when it is desired to observe an emission spectra from the object, the individual light sources 406 of the shadow-less light 404 selectively shine through a spectral filter 408 (FIG. 9) that blocks the wavelength of the emission spectra to be observed, such that the shadow-less light source does not interfere with the observance of that emitted wavelength. In some embodiments, the individual light sources are white light emitting diodes (LED). In some embodiments, the individual light sources are white light emitting diodes (LED) that are filtered by a 775 nm low-pass filter. In another embodiment, the low-pass filter may be replaced with a polarizer, or may be used in conjunction with the filter.

In a particular embodiment, the light source 400 is a fluorescence-friendly shadow-less surgical light, which can provide white light surgical illumination and florescence illumination without leaking frequencies overlapping with fluorescence emission. This shadow-less light offers both well-rendered surgical illumination (looks like white light to naked light) and fluorescence excitation at the same time. In one embodiment, such light source comprises a plurality of white light emitting diodes (LED) coupled with Notch Filters that are Optical Filters that selectively reject a portion of the spectrum, while transmitting all other wavelengths. With the notch the frequencies overlapping with fluorescence emission, which are emitted by white LEDs, are rejected. It should be appreciated that in some cases edge filters can be used to achieve similar results in blocking the frequencies overlapping with fluorescence emission. In one example, the shadow-less light source comprises a plurality of white light emitting diodes (LED) that is filtered by a 775 nm low-pass filter. It should be appreciated that thin films or other devices may play similar role as notch filters or edge filters in the fluorescence-friendly shadow-less surgical light. In one aspect, the shadow-less light 400 may comprise an array of white lamps with edge filters or notch filters. In another embodiment, the spectral filters may be replaced with polarizers, or may be used in conjunction with the filters.

In some embodiments, the light source is a traditional projector (lamp based) or digital projector (LED-based) selectively used in conjunction with spectral filters or polarizers (as described with other light sources). The projector can also selectively project spatial frequencies (i.e., provide patterned illumination). The spectral filters can be in a filter wheel as already described. The projector beneficially provides a well-defined illumination area. The projector can be set to project any desired wavelength of light and can project without brighter and dimmer areas (i.e., provides consistent light).

Figure 10:
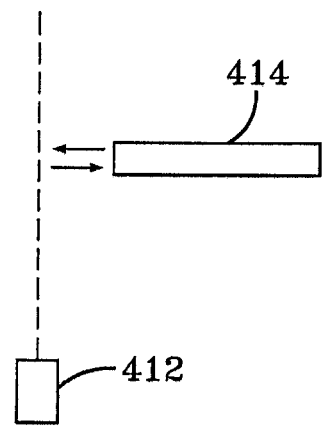
FIG. 10 is a general schematic view of a laser and laser diffuser light source, shown with the diffuser out of the path of the laser in accordance with the concepts of the present invention.
Figure 11:
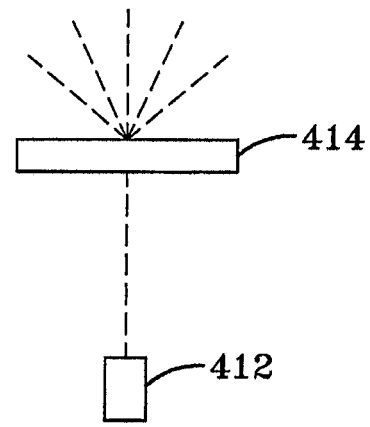
FIG. 11 is a general schematic view of a laser and laser diffuser light source, shown with the diffuser in the path of the laser in accordance with the concepts of the present invention.

With reference to FIGS. 10 and 11, in another embodiment, the light source 400 comprises a laser diode 412 and a diffuser 414 movable to be selectively interposed between the laser diode 412 and the object. Without the diffuser 414 interposed, the laser diode 412 simply shines a focused beam of light, while, with the diffuser 414 interposed, the laser shines over a greater surface area and is suitable for general illumination. In some embodiments this can allow for switching between laser aiming and night vision (with diffuser out of light path) or fluorescence-guided treatment (with diffuser in light path). In addition, the laser diode with diffuser 400 may also use a filter. In addition, the laser diode 400 may also be pulsed, or frequency modulated to reduce the average amount of light energy delivered.

Pulsing of Light

As seen in FIGS. 9 and 10, in some embodiments, the light source 400 may comprise a pulsed light source, or may utilize frequency modulation or pulse-duration modulation. In one aspect, the detector 120 may detect signals of a given frequency or spectrum, and the light source 400 may correlate the detected signal with the frequency modulation and pulse-duration modulation. In one aspect, the light source 400 may modulate the emitted light using an electro-optic modulator, optical chopper, or the like. Alternatively, if the light source 400 comprises one or more light emitting diodes (LED) the light source 400 may operate to adjust the intensity of light being output by adjusting the frequency of the AC (alternating current) that is supplied to power the LEDs.

Figure 6:
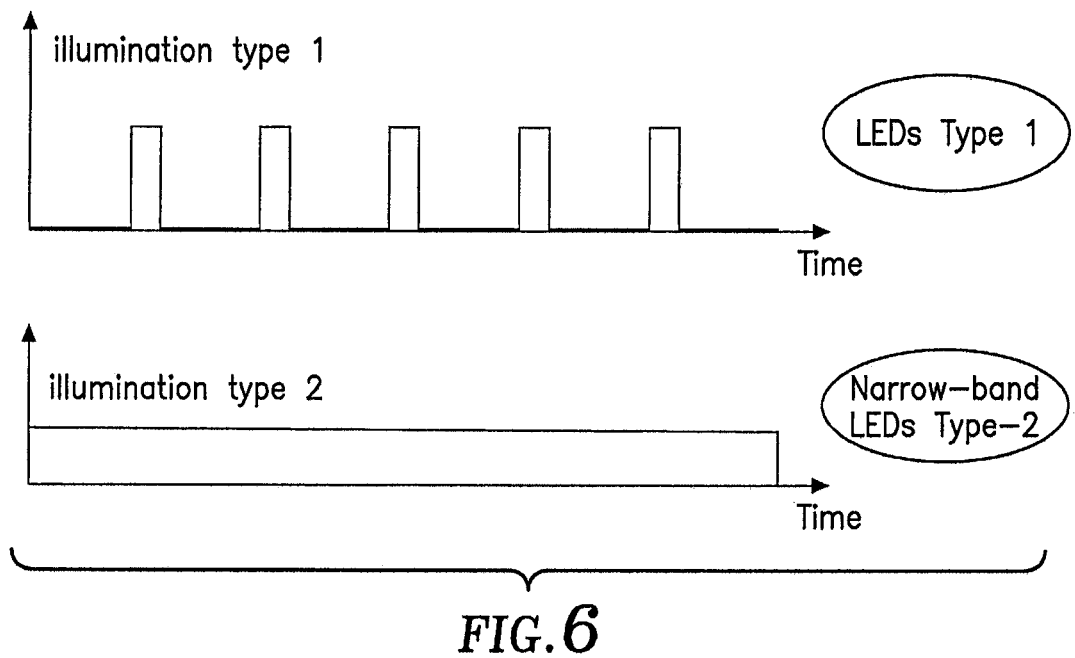
FIG. 6 is a graph showing a plurality of illumination pulse patterns output by a light source for use with the imaging and display system in accordance with the concepts of the present invention.

Specifically, as shown in FIG. 6, the DC component of the light source 400 detected by the goggle system 100 are the fluorescence image type-2, and the AC component of the light detected by the goggle system 100 are florescence image type-2. The goggle system 100 may use a 2-camera setup or a 4-camera setup. The goggle system 100 is configured to detect the signals, correlated with the frequency modulation or pulse-duration modulation. Various ways of modulating the light may be used, such as an electro-optic modulator, an optical chopper, or the like. If LEDs are used, the illumination output by the light source 400 can be modulated by supplying AC current of desirable frequency through the LEDs. A lock-in amplifier may be used by the system 100. It should be appreciated that light bulbs, lamps, laser diodes, lasers or the like could be used instead of LED based light source 400.

Figure 7:
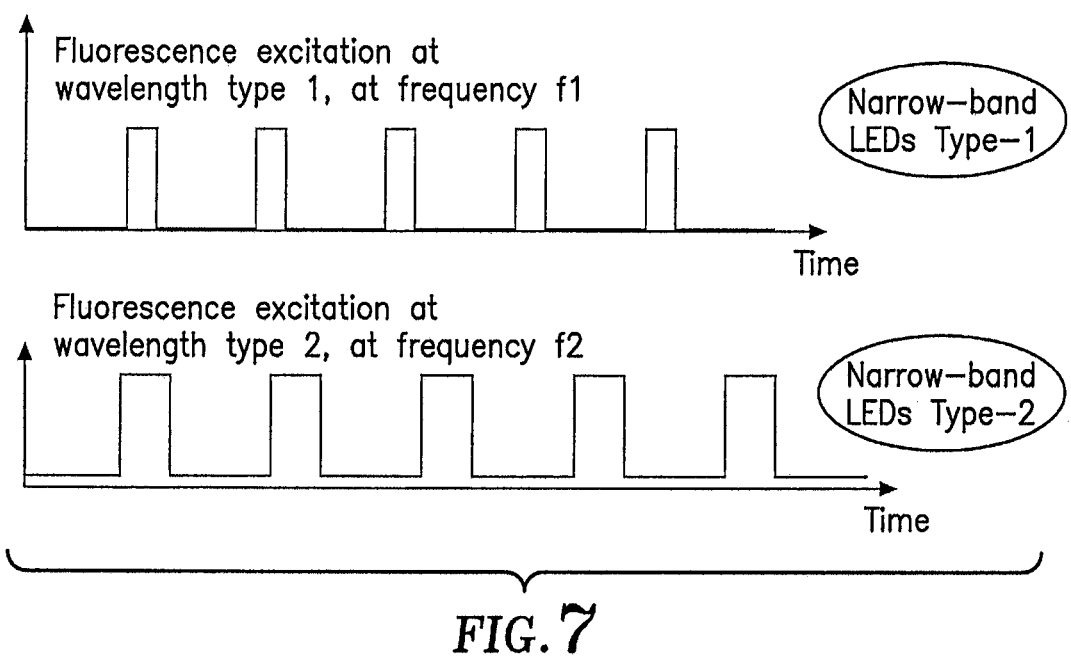
FIG. 7 is a graph showing another plurality of illumination pulse patterns output by the light source in accordance with the concepts of the present invention.

Furthermore, as shown in FIG. 7, the frequency component of the light source 400 designated f1, which is detected by the goggle system 100 will be the fluorescence image type-1, and the frequency component of the light designated f2 that is detected by the goggle system 100 is the fluorescence image type-2. The goggle system 100 may use a 2-camera setup or 4-camera setup, and the goggle system 100 will detect the signals, correlated with the frequency modulation or pulse-duration modulation. Possible ways of modulating the light may comprise electro-optic modulator, optical chopper, or the like. In addition, if LEDs are used, the illumination output by the light source 400 can be modulated by supplying AC current of desirable frequency through the LEDs. In addition, a lock-in amplifier may be used by the system 100. It should be appreciated that light bulbs, lamps, laser diodes, lasers or the like could be used instead of LED based light source 400.

It is also contemplated that the system 100 includes a microphone 480 and a speaker 490 to enable verbal communication between the various systems 100A-X and other computer systems (i.e. tablet computers, smart phones, desktop computers), and the like using the communication network 260.

Thus, with the structural arrangement of the various components of the imaging and display system 100 set forth above, the following discussion will present various embodiments of the system 100 for executing specific functions.

Polarization

The system 100, as previously discussed by use of the polarizer 152 in a convertible or selective manner, such that when polarization is invoked in a first state, the detector 120 provides polarization-gated imaging, polarization difference imaging, spectral-difference polarization imaging, Muellar matrix imaging.

For example, the system 100 may also use traditional division of time techniques, as well as tunable liquid crystal polarization filters or division of focal plane technology (e.g. Moxtek micropolarizer arrays).

Networked System

As previously discussed, each imaging and display system 100 includes the detector 150 and a communication interface 250, which allows a plurality of systems 100A-X to communicate various data with one another and/or with one or more remote computing devices. It should be appreciated that the system 100 may be configured to form ad-hoc networks between each one of the individual systems 100A-X, or may be configured to join any exiting wireless communication network, such as a cellular data network, radio-frequency communication, wireless LAN, wireless PAN, WiFi or Bluetooth network for example. As previously discussed, each system 100 has the ability to be a sender of data and a recipient of data. It should be appreciated that system 100 can send data to any type of display unit, including other non-wearable display and wearable display units, to enable visualization of content displayed at system 100.

In one embodiment, the detector 120 of one system 100 may capture image or video data that is transferred over the network to one or more other systems 100A-X or any other computing device (i.e. tablet, computer, smartphone) that are connected to the communication network. Such image transfer may occur simultaneously between the systems 100A-X in real-time or in near real-time. The real-time or near real-time transmission of image or video data, such as viewing an patients, from one system 100 may be used by recipients of the image or video data at one or more other users of the system 100, or any other users of wearable displays, or any other users of other computer systems connected to the network, in order to analyze and provide medical guidance based on the transferred images. In addition, such networked systems 100 allow the point-of-view or field-of-view of the system 100 at which the image originates to be relayed to the other networked systems 100, or other wearable displays or computing devices, to facilitate medical training, diagnosis, and treatment. As a result, the point of view or field of view of one system 100 can be presented to other networked systems 100 or computing systems.

In addition, the network of systems 100 may also be used to enable the visualization of educational content, including but not limited to medical training, surgical training and the like.

GPS

When the system 100 is configured with a GPS peripheral 350, the system 100 is able to provide navigational information. As such, the system 100 may be able to report the location of the device 100, communicate the location to another remote location over the communication network to which the system 100 is connected. Furthermore, all navigational information can be used by the system 100 to tag all data that is gathered by the system 100, such as images collected for example.

Microscope Imaging

The system 100 may also include microscopic imaging features. In one aspect, the detector 120 may include the necessary optics to provide microscopic imaging. In one aspect, the detector 120 may have built-in optics to conduct microscopic imaging or may have interchangeable optical components for microscopic imaging. In another aspect, the microscope may be provided as a separate peripheral 350 that is coupled to the peripheral interface 300, such that the image supplied by the microscope may be presented on the display or communicated through the network other systems 100 and networked devices, as previously discussed.

Medical Training

In one aspect, the memory unit of the system 100 may store software to simulate a medical training procedure that is based on virtual reality or augmented reality. Two dimensional or three dimensional images or video may be stored at the memory unit of the system 100, or in a remote server coupled to the network to which the system 100 is connected, which enables visualization of educational content, such as medical training and surgical training.

In another aspect, the training software may include audio-visual training tutorials with step-by-step instructions for carrying out particular procedures via the display 110. In addition, the tutorials may outline tasks for how to prepare for an examination, how to operate ultrasound, and how to position a patient. Ultrasound techniques, such as how to manipulate the ultrasound probe and use the keyboard functions of the ultrasound system may be included. The tutorials may also include various examination protocols; reference anatomy information with reference ultrasound images; procedures for how to make a diagnosis; and procedures for how to treat patients and treatment tutorials may be included.

Alternatively, the system 100 may be worn by an instructor, such as a teaching surgeon, to provide teaching and instruction, such as the teaching of new surgical procedures and techniques. As such, the point of view/field of view, as captured by the detector 120 of the system 100 worn by the instructor is transmitted via the communication network 260 to one or more students that are also wearing the system 100 for presentation on their wearable display 110. In addition, the instructor's point of view/field of view may be transmitted to any other local or remote display, either wearable or non-wearable. In one aspect, a stereoscopic imaging and display system 100 enable capturing the stereoscopic view of the teacher surgeon, and transmit to other students also wearing stereoscopic imaging and display systems 100, in real time or near real time. The depth perception of stereoscopic images and video provide a more realistic training experience of medical procedures such as surgeries. Furthermore, the students wearing stereoscopic imaging and display systems 100 are able to see the training procedures conducted by the teacher surgeon with the teacher's point of view and field of view with depth perception, in real time or near-real time, which is more realistic than conventional method. Moreover, when the students are performing similar procedures, the teacher wearing a stereoscopic imaging and display system 100 will be able to visualize the field-of-view of one or more students. In one aspect, the teacher can monitor students' performance by displaying different student's stereoscopic view in a picture-in-picture format, or display several windows of different students concurrently. Thus, the pluralities of stereoscopic imaging and display systems form a network for teaching medical procedures and non-medical procedures, with a depth-perception and viewpoint-sharing.

Selective Bleed-Through

In one aspect, the light source 400 may have components that overlap with emission spectra, referred to as bleed-through components. The bleed-through components can be tunable to achieve desirable level of background. For example, in the case of indocyanine green dye, if the emission filter is an 820 nm long-pass filter, the component of illumination is >820 nm will pass through the emission filter (if emission filter is 820 nm long pass filter) and become the background, or the bleed-through component. The illumination could have both 780 nm LEDs for fluorescence excitation and 830 nm LEDs for bleed-through. By changing the intensity of the 830 nm LEDs, the level of background can be adjusted, which is useful in a variety of situations.

Medical or Surgical Guidance

Figure 4:
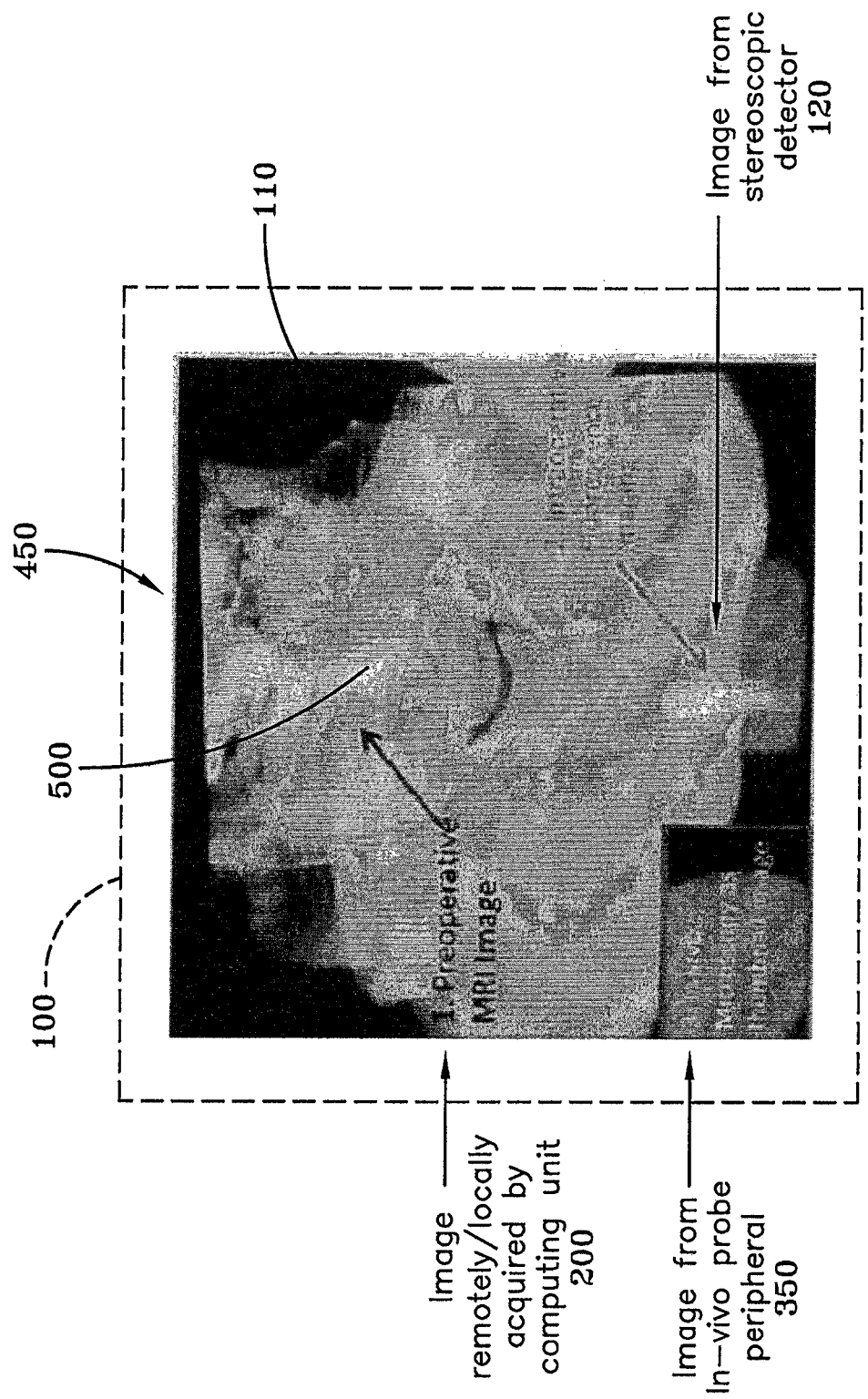
FIG. 4 is a schematic view of a composite image of a pre-operative surgical navigation image, an intra-operative image, and an in-vivo microscopy image that are simultaneously presented on the display of the imaging and display system for guiding medical interventions in accordance with the concepts with the present invention.

Thus, with the components of the system 100 set forth, the particular medical guidance functions enabled by the system will now be described in detail. Thus, once the system has acquired the surgical navigation pre-operative images, the intra-operative images (e.g. fluorescence images), and the in-vivo, high-resolution imaging/sensing microscopy images (e.g. fluorescence microscopy images), the previously discussed tracking and registration techniques are applied to the images. As a result, all three image types are integrated, or superimposed, simultaneously together, so as to form a composite, co-registered image 450 for presentation on the display 110 of the wearable system 100, as shown in FIG. 4. It should be appreciated that the detector 120 may provide stereoscopic imaging using the cameras 120A-B, as previously discussed. This, allows a 3-dimensional image to be displayed for viewing by the surgeon via the wearable display 110, which simulates natural human vision, thereby allowing depth perception that is critical in the guidance of medical assessments during surgeries.

The co-registered composite image 450 is configured, whereby the pre-operative image data, such as MRI (magnetic resonance imaging) data for example, is segmented and processed into, and rendered, as a 3-dimensional model having a plurality of 3D surfaces. It should be appreciated that any suitable segmentation process may be used, including: either automatic, manual or semi-automatic segmentation processes. In addition, segmentation can also be based on thresholding methods, clustering methods, compression-based methods, histogram-based methods, edge detection methods, region-growing methods, split-and-merge methods, partial differential equation-based methods, parametric methods, level set methods, fast marching methods, graph portioning methods, watershed transformation methods, model based segmentation methods, multi-scale segmentation methods, trainable segmentation methods, and any combination thereof.

In one example, threshold based segmentation and manual segmentation may be used prior to 3D rendering of the pre-operative images. In addition, one may use histogramming with a programmable threshold, Otsu segmentation for automatic thresholding, and a two-step drawing tool where regions are manually selected and then grouped using a clustering algorithm. Alternatively, manual region selection may be conducted. In another example, one may convert the rendered volume of the MRI images into a surface mesh, and save the mesh as an object file. Histogram thresholding may be used to create inner and outer volumes of 3D renderings, where the inner volume represents one organ, and the outer volume represents another organ.

Using tracking technologies, such as those previously discussed, the 3D pre-operative model based on the MRI or other tomographic data is mapped to the physical dimensions of the patient 500, as shown in FIG. 4 who is undergoing the surgical procedure. That is, the mapping process results in the organs or other physical characteristic identified by the pre-operative 3D model of the patient to be correlated with the corresponding organs of the patient 500 undergoing the surgical procedure. It should be appreciated that the pre-operative data may be acquired remotely by the system 100 via the communication network 260 or locally by a portable memory unit configured to be coupled to or in communication with the peripheral interface 300. In one aspect, the pre-operative image data may comprise any 3D volumetric data or tomographic image data. In addition, the pre-operative data used by the system 100 may comprise point cloud data, surface rendered data or meshed data, MRI (magnetic resonance image) image data, computed tomography (CT) image data, positron emission tomography (PET) image data, single-photon emission computed tomography (SPECT), PET/CT, SPECT/CT, PET/MRI, gamma scintigraphy, X-ray radiography, ultrasound, and the like.

After the pre-operative image data is mapped to the patient 500, intra-operative imaging, such as fluorescence images, acquired by the detector 120 in real-time or near real-time shows where a particular lesion or surgical site of interest is during the surgical procedure, and is added to the composite image 450. Thus, the intra-operative fluorescence image complements the 3D pre-operative MRI image that is displayed by the system 100. It should also be appreciated that the intra-operative fluorescence imaging also guides further assessment of small lesions and other tissue structures using the in-vivo microscopy hand-held probe, as previously discussed. In particular, the operator or surgeon wearing the system 100 uses the in-vivo microscopy hand-held probe to closely examine the diseased tissue or area, which is shown by the intra-operative fluorescence imaging.

The high-resolution microscopic image from the hand-held microscopy probe is also shown on the wearable display 110 in real-time as an inset or picture-in-picture image, as shown in FIG. 4. As such, FIG. 4 displays the ability of the system 100 to present via the display 110 pre-operative MIll-based surgical navigation imaging, intra-operative fluorescence imaging, and in-vivo microscopy imaging. This allows the user of the system 100 to conveniently identify the diseased tissue or lesion in the patient, while improving the diagnostic accuracy and decreasing the time needed for assessment.

It should be appreciated that while the discussion of the system 100 presented above enables the display 110 to show pre-operative images, intra-operative images, and in-vivo microscopy images together as a composite image 450 each having various levels of transparency relative to one another, any combination of one or more of the image types may be presented on the display 110. For example, only pre-operative surgical navigation images and intra-operative fluorescence images may shown together on the display 110; or only intra-operative images may be shown on the display 110.

It should also be appreciated that the system 100 may be configured, such that multiple intra-operative modalities are offered simultaneously, at the same time. For example, intra-operative fluorescence imaging and polarization imaging, as previously discussed, may be provided by the system 100 at the same time. Similarly, intra-operative fluorescence imaging and color imaging may be provided at the same time by the system 100.

In another aspect, the system 100 may be utilized to perform gastrointestinal examinations, such as colonoscopies or esophagus examinations. In such case, the surgical navigation pre-operative image is based on a CT colonoscopy (virtual colonoscopy) image, the intra-operative imaging is acquired by an endoscope, and the high-resolution in-vivo microscopy sensing is achieved by an endomicroscopy probe. In addition, the system 100 may include a therapy module 350 for attachment to the peripheral interface 300 that performs the image-guided endoscopic surgery. As such, the system 100 allows the position of the endoscope to be accurately tracked and displaced relative to the 3D rendered models generated based on the CT colonoscopy pre-operative image. Thus, surgical navigation can guide the assessment of a lesion using the endoscope. Additionally, suspicious lesions can be assessed by the in-vivo endo-microscope probe to examine the microscope and pathological details.

It should be appreciated that in addition to the types of displays 110 previously discussed, the display 110 may also enable the side-by-side display of images, and may also include: anaglyph displays, polarized 3D displays, active shutter 3D displays, interference filter 3D display systems, and the like. In addition, the display 110 may also comprise non-stereoscopic display types as well. In addition, the display 110 may comprise LCD (liquid crystal) microdisplays, LED (light emitting diode) microdisplays, organic LED (OLED) microdisplays, liquid crystal on silicon (LCOS) microdisplays, retinal scanning displays, virtual retinal displays, optical see through displays, video see through displays, convertible video-optical see through displays, wearable projection displays, and the like. In addition the display 110 may utilize a holographic display.

In addition, the detector 120 configurations previously discussed with regard to FIGS. 3A-E may be used to provide the intra-operative images, such as the fluorescence images, used for generating the composite image 450 for presentation on the display 110 by the system 100. For example, the cameras 120A-B may be configured to provide stereoscopic fluorescence imaging.

In addition, the light source 400 is used during intra-operative imaging, such as fluorescence imaging, and may include but is not limited to: a non-coherent light source, such as a Xenon lamp, a halogen lamp and LEDs. In addition, coherent light sources may be used, such as lasers, and laser diodes. Furthermore, various fluorescence tracers may be used to initiate fluorescence at the surgical site or tissue of interest 130 may be used by the system 100 for use in different light source 400 spectra, including the UV (ultra-violet) range, visible range, and infrared (IR) range may be used with the system 100. In one aspect, near-infrared (NIR) fluorescence imaging may be performed using indocyanine green as a fluorescence tracer.

In addition to intra-operative fluorescence imaging, other types of intra-operative imaging may be performed, including: polarization imaging, absorption imaging, oxygen saturation information imaging, or any combination thereof.

Furthermore, intra-operative imaging may be performed for any suitable surgical procedure, such as open surgery, endoscopic surgery, laparoscopic surgery, or any combination thereof.

It should also be appreciated that the intra-operative imaging probe used to acquire the intra-operative images may comprise an ultrasound probe, an endoscope, a laparoscope, a bronchoscope and the like.

It should also be appreciated that in-vivo microscopic imaging may be performed by any suitable in-vivo microscopy probe, such as an in-vivo fluorescence/reflectance microscopy probe. In addition, various in-vivo microscopy detection and techniques may be used by the system 100, including color microscopy, reflectance microscopy, fluorescence microscopy, oxygen-saturation microscopy, polarization microscopy, infrared microscopy, interference microscopy, phase contrast microscopy, differential interference contrast microscopy, hyperspectral microscopy, total internal reflection fluorescence microscopy, confocal microscopy, non-linear microscopy, 2-photon microscopy, second-harmonic generation microscopy, super-resolution microscopy, photoacoustic microscopy, structured light microscopy, 4Pi microscopy, stimulated emission depletion microscopy, stochastic optical reconstruction microscopy, ultrasound microscopy, and any combination thereof.

In addition, the in-vivo probe may comprise a handheld \ that has not yet reached the microscopic resolution. Non-microscopic imaging methods, which may be used by the in-vivo probe 350 may include reflectance imaging, fluorescence imaging, Cerenkov imaging, polarization imaging, ultrasound imaging, radiometric imaging, oxygen saturation imaging, optical coherence tomography imaging, infrared imaging, thermal imaging, photoacoustic imaging, spectroscopic imaging, hyperspectral fluoroscopy imaging, gamma imaging, x-ray computed tomography imaging, or any combination thereof. It should also be appreciated that the in-vivo microscopy probe may comprise an endoscope, a laparoscope, a bronchoscope, an angioscope, a catheter for angiography.

In another aspect, the in-vivo probe may comprise a non-imaging device, such as a sensing device, including a handheld spectrophotometer or fiber-based spectrometers. Using the in-vivo sensing probe, various spectroscopies may be realized, such as various optical spectroscopies, absorption spectroscopy, fluorescence spectroscopy, Raman spectroscopy, coherent anti-Stokes Raman spectroscopy (CARS), surface-enhanced Raman spectroscopy, Fourier transform spectroscopy, Fourier transform infrared spectroscopy (FTIR), multiplex or frequency-modulated spectroscopy, x-ray spectroscopy, attenuated total reflectance spectroscopy, electron paramagnetic spectroscopy, electron spectroscopy, gamma-ray spectroscopy, acoustic resonance spectroscopy, Auger spectroscopy, cavity ring down spectroscopy, circular dichroism spectroscopy, cold vapour atomic fluorescensce spectroscopy, correlation spectroscopy, deep-level transient spectroscopy, dual polarization interferometry, EPR spectroscopy, force spectroscopy, Hadron spectroscopy, Baryon spectroscopy, meson spectroscopy, inelastic electron tunneling spectroscopy (IETS), laser-induced breakdown spectroscopy (LIBS), mass spectroscopy, Mossbauer spectroscopy, neutron spin echo spectroscopy, photoacoustic spectroscopy, photoemission spectroscopy, photothermal spectroscopy, pump-probe spectroscopy, Raman optical activity spectroscopy, saturated spectroscopy, scanning tunneling spectroscopy, spectrophotometry, time-resolved spectroscopy, time-stretch spectroscopy, thermal infrared spectroscopy, ultraviolet photoelectron spectroscopy (UPS), video spectroscopy, vibrational circular dichroism spectroscopy, x-ray photoelectron spectroscopy (XPS), or any combination thereof.

Based on the foregoing, the advantages of the present invention are readily apparent. The main advantage of this system to provide a plurality of ways to guide medical procedures, such as surgical procedures, through surgical navigation (e.g. pre-operative imaging), intraoperative imaging and high-resolution in-vivo imaging/sensing (e.g. microscopy) using a single wearable system. Still another advantage of the present invention is that medical information at all scales is available at the same time for viewing by a surgeon, whereby surgical navigation provides whole-body information based on MRI or CT imaging; intraoperative imaging offers real-time information for the organ of interest; and microscopy offers microscale information, which is more convenient and faster than conventional pathology reporting techniques. Another advantage of the present invention is that the wearable system is easy to wear and use, and is user-friendly to operate. Yet another advantage of the present invention is that the depth perception (i.e. stereoscopic vision) offered by the system is beneficial in guiding surgery, which surpasses the performance of planar imaging and 2D monitor display. Another advantage of the present invention is that the wearable device provides a way to correlate surgical navigation, intraoperative imaging and high-resolution imaging together, via accurate tracking and image registration techniques. Yet another advantage of the present invention is that the system provides wireless communication, which allows the wearable device to communicate with multiple communication devices and wearable devices remotely and locally; whereby the remote user of the system has the option to view stereoscopic information and talk to local clinicians in near real-time. Another advantage of the present invention is that the wearable device is self-contained, which facilitates its use in rural areas, developing countries, and in first responder and security/defense applications. Still another advantage of the present invention is that the wearable device along with other remotely located wearable devices may be used for medical training where the actual medical information viewed by the surgeon can be simultaneously viewed by students. Another advantage of the present invention is that the wearable device may be low cost; may be used in any diverse surgical settings, such as veterinary medicine. Another advantage of the present invention is that a platform technology is provided by the system, which can be used for nearly all medical interventions where radiographic findings are important.

Thus, it can be seen that the objects of the present invention have been satisfied by the structure and its method for use presented above. While in accordance with the Patent Statutes, only the best mode and preferred embodiment has been presented and described in detail, it is to be understood that the present invention is not limited thereto or thereby. Accordingly, for an appreciation of the true scope and breadth of the invention, reference should be made to the following claims.

What is claimed is:

1. A system for capturing images of a target of interest and displaying captured images to a user that is engaging the target of interest, comprising:
    a wearable display configured to be that is worn on a head of the user as the user engages the target of interest and is configured to display a field of view of an intraoperative image to the user in real-time as the user engages the target of interest via the wearable display, wherein the field of view includes the image data of the intraoperative image displayed in real-time as the user engages the target of interest;
    a detector that is coupled to the wearable display and is configured to capture an imaging field of view of the target of interest in real-time;
    a computing device configured to:
        filter image data from the imaging field of view of the target of interest that is included in the field of view,
        adjust the imaging field of view of the target of interest as captured by the detector to the field of view of the target of interest as displayed to the user by the wearable display in real-time based on the filtered image data as included in the field of view thereby enabling the user to view whole-body data and segmented data of an area of interest in real-time as the user engages the target of interest, and
        instruct the wearable display to display to the user in real-time the field of view based on the filtered image data, wherein the field of view that is thereby displayed to the user by the wearable display in real-time is a total field of view of the user thereby enabling the user to view the whole-body data of the target of interest and the segmented data of the area of interest in real-time as the user engages the target of interest.

2. The system of claim 1, wherein the wearable display is further configured to:
    display a portion field of view of the intraoperative image in real-time to the user as the user engages the target of interest via the wearable display, wherein the portion field of view that is thereby displayed to the user by the wearable display is less than the total field of view of the user.

3. The system of claim 2, wherein the computing device is further configured to:
    filter image data from the imaging field of view of the target of interest that is included in the portion field of view;
    adjust the imaging field of view of the target of interest as captured by the detector to the portion field of view of the target of interest as displayed to the user by the wearable display in real-time based on the filtered image data as included in the portion field of view thereby enabling the user to view the whole-body data and the segmented data of an area of interest in real-time as the engages the target of interest; and instruct the wearable display to display to the user in real-time the portion field of view based on the filtered image data, wherein the portion field of view that is thereby displayed to the user by the wearable display in real-time is less than the total field of view of the user thereby enabling the user to view the whole-body data of the target of interest and the segmented data of the area or interest in real-time as the user engages the target of interest.

4. The system of claim 1, wherein the computing device is further configured to:
   filter image data from the imaging field of view of the target of interest that is within a zoom level associated with a zoom field of view, wherein the zoom level indicates the image data that is to be filtered from the imaging field of view to generate the zoom field of view that encompasses image data that is within the zoom level;
   adjust the imaging field of view of the target of interest as captured by the detector in real-time to the zoom level field of view of the target of interest based on the filtered image data that is within the zoom level; and
   instruct the wearable display to display to the user the zoom level field of view that is thereby displayed in real-time to the user by the wearable display, wherein the zoom level field of view is less than the imaging field of view of the detector.

5. The system of claim 2, wherein the computing device is further configured to:
   select a zoom level from a plurality of zoom levels that image data is to be filtered from the imaging field of view of the target of interest that is within the selected zoom level; and
   adjust the zoom level in real-time to the selected zoom level to adjust the image data that is filtered from the imaging field of view of the target of interest that is within the selected zoom level thereby enabling the user to view the segmented data of the area of interest of the selected zoom level and the whole-body data of the target of interest in real-time.

6. The system of claim 1, wherein the computing device is further configured to:
   filter image data from the imaging field of view of the target of interest that is within a resolution associated with a resolution field of view, wherein the resolution indicates the image data is to be filtered from the imaging field of view to generate the resolution field of view that encompasses image data that is within the resolution;
   adjust the imaging field of view of the target of interest as captured by the detector in real-time to the resolution field of view of the target of interest based on the filtered image data that is within the resolution thereby enabling the user to view the whole-body data and the segmented data of an area of interest in real-time as the engages the target of interest; and
   instruct the wearable display to display to the user the resolution field of view that is thereby displayed in real-time to the user by the wearable display, wherein the resolution field of view is less than the imaging field of view of the detector.

7. The system of claim 6, wherein the computing device is further configured to:
   select a resolution from a plurality of resolutions that image data is to be filtered from the imaging field of view of the target of interest that is within the selected resolution; and
   adjust the resolution in real-time to the selected resolutions to adjust the image data that is filtered from the imaging field of view of the target of interest that is within the selected resolution thereby enabling the user to view the segmented data of the area of interest of the selected resolution level and the whole-body data of the target of interest in real-time.

8. The system of claim 1, wherein the computing device is further configured to:
   filter image data from the imaging field of view of the target of interest that is within a working distance associated with a working distance field of view, wherein the working distance indicates the image data that is to be filtered from the imaging field of view to generate the working distance field of view that encompasses image data that is within the working distance;
   adjust the imaging field of view of the target of interest as captured by the detector in real-time to the working distance field of view of the target of interest based on the filtered image data that is within the working distance thereby enabling the user to view the whole-body data and the segmented data of an area of interest in real-time as the engages the target of interest; and
   instruct the wearable display to display to the user the working distance field of view that is thereby displayed in real-time to the user by the wearable display, wherein the working distance field of view is less than the imaging field of view of the detector.

9. The system of claim 8, wherein the computing device is further configured to:
   select a working distance from a plurality of working distances that image data is to be filtered from the imaging field of view of the target of interest that is within the selected working distance; and
   adjust the working distance in real-time to the selected working distance to adjust the image data that is filtered from the imaging field of view of the target of interest that is within the selected working distance thereby enabling the user to view the segmented data of the area of interest of the selected working distance level and the whole-body data of the target of interest in real-time.

10. The system of claim 1, further comprising:
    a filter configured to filter the image data of the imaging field of view of the target of interest as captured by the detector to image data that is within a first frequency spectrum.

11. A system for capturing images of a target of interest and displaying captured images to a user that is engaging the target of interest, comprising:
    a wearable display configured to be worn on a head of a user as each user engages the target of interest with the wearable display configured to display to the user an image of the target of interest in real-time as the user engages the target of interest;
    a detector coupled to the wearable display and configured to capture image data associated with the field of view of the target of interest for the detector in real-time;
    a computing device associated with the wearable display and configured to:
       engage in communication with a corresponding networked computing device from a plurality of networked computing devices to enable image data captured by the detector of the wearable display to be communicated to each other networked computing device, and transmit the image data captured by the detector of the wearable display in real-time to each other networked computing device thereby enabling the image data captured by the detector of the wearable display in real-time to be displayed by each networked computing device in real-time.

12. The system of claim 11, the computing device associated with the wearable display is further configured to:
engage in communication with each corresponding networked computing device to enable the image data of a field of view as captured by the detector of the wearable display to be communicated to each other networked computing device; and
transmit the image data of the field of view captured by the detector of the wearable display in real-time to each other networked computing device thereby enabling the image data of the field of view as captured by the detector of the wearable display in real-time to be displayed to each networked computing device in real-time, wherein the field of view of the detector of the wearable device is the field of view displayed to each networked computing device in real-time.

13. The system of claim 12, the computing device associated with the wearable display is further configured to:
engage in communication with each corresponding networked computing device to enable image data of the field of view captured by the detector of the wearable display to be communicated to each other networked computing device; and
transmit the image data of the field of view as captured by the detector of the wearable display in real-time to each other networked computing device thereby enabling image data of the field of view as captured by the detector of the wearable display in real-time to be displayed to each networked computing device in real-time; and
provide a communication stream with each corresponding networked computing device for each corresponding user of each corresponding networked computing device to communicate with each other user of each other corresponding networked computing device as the user of the wearable display engages the target of interest thereby enabling each user of each corresponding networked computing device to communicate as the image data of the field of view of the detector of the wearable display is displayed to each networked computing device in real-time.

14. The system of claim 13, wherein the computing device of the wearable display is further configured to receive instructions from each corresponding networked computing device to adjust the field of view of the detector of the wearable display thereby enabling each user of each corresponding networked computing device to view image data that is adjusted based on the adjusted field of view of the detector of the wearable display as the user of the wearable display engages the target of interest.

15. The system of claim 11, wherein:
the wearable display that is configured to be worn on the head of the user as the user engages the target of interest and is configured to display a portion field of view to the user in real-time as the user engages the target of interest via the wearable display, wherein the portion field of view that is thereby displayed to the user by the wearable display is less than a total field of view of the user;
the detector that is coupled to the wearable display and is configured to capture an imaging field of view of the target of interest in real-time; and
the computing device is configured to:
filter image data from the imaging field of view as the target of interest that is included in the portion field of view,
adjust the imaging field of view of the target of interest as captured by the detector to the portion field of view of the target of interest as displayed to the user by the wearable display based on the filtered image data as included in the portion field of view,
engage in communication with each corresponding networked computing device associated from the plurality of networking computing devices to enable the portion field of view of the target of interest as captured by the detector of the wearable display to be communicated to each other networked computing device, and
transmit the portion field of view of the target of interest captured by the detector of the wearable display in real-time to each other networked computing device thereby enabling the image data captured by the detector of the wearable display in real-time to be displayed by each networked computing device in real-time.

16. The system of claim 11, further comprising:
a plurality of wearable displays with each respective wearable display configured to be worn on a head of a corresponding user as each user engages the target of interest with wearable display and configured to display to the user an image of the target of interest in real-time as the user engages the target of interest;
a plurality of detectors with each detector coupled to a corresponding wearable display and configured to capture image data associated with a corresponding field of view of the target of interest for each corresponding detector in real-time;
a plurality of computing devices with each computing device associated with a corresponding wearable display, each corresponding wearable display being configured to engage in communication with a corresponding computing device associated with the corresponding wearable display to enable image data captured by each corresponding detector in real-time to be communicated to each other computing device in real-time.

17. The system of claim 16, wherein the plurality of computing devices is further configured to:
engage in communication with each corresponding networked computing device from the plurality of networked computing devices to enable image data captured by each corresponding detector of each corresponding wearable device to be communicated to each other networked computing device; and
transmit the image data captured by each corresponding detector of each corresponding wearable display in real-time to each other networked computing device thereby enabling the image data captured by each corresponding detector of each corresponding wearable display in real-time to be displayed by each networked computing device in real-time.

18. The system of claim 17, wherein the plurality of computing devices is further configured to:
engage in communication with each corresponding networked computing device to enable the image data of a field of view as captured by each corresponding detector of each corresponding wearable display to be communicated to each other networked computing device; and transmit the image data of the field of view captured by each corresponding detector of each corresponding wearable display in real-time to each other networked computing device thereby enabling the image data of the field of view as captured by each corresponding detector of each corresponding wearable display in real-time to be displayed to each networked computing device in real-time, wherein the field of view of each corresponding detector of each corresponding wearable device is the field of view displayed to each networked computing device in real-time.

19. The system of claim 18, wherein the plurality of computing devices is further configured to:

engage in communication with each corresponding networked computing device to enable image data of the field of view captured by each corresponding detector of each corresponding wearable display to be communicated to each other networked computing device;

transmit the image data of the field of view as captured by each corresponding detector of each corresponding wearable display in real-time to each other networked computing device thereby the enabling data of the field of view as captured by each corresponding detector of each corresponding wearable display in real-time to be displayed to each networked computing device in real-time; and provide a communication stream with each corresponding networked computing device for each corresponding user of each corresponding networked computing device to communicate with each other user of each other corresponding networked computing device as each user of each corresponding wearable display engages the target of interest thereby enabling each user of each corresponding networked computing device to communicate as the image data of the field of view of each corresponding detector of corresponding wearable display is displayed to each networked computing device in real-time.

20. The system of claim 19, wherein each computing device of each corresponding wearable display is further configured to receive instructions from each corresponding networked computing device to adjust the field of view of each corresponding detector of each corresponding wearable display thereby enabling each user of each corresponding networked computing device to view image data that is adjusted based on the adjusted field of view of each corresponding detector of each corresponding wearable display as each user of each corresponding wearable display engages the target of interest.

* * * * *